(12) United States Patent
Imai et al.

(10) Patent No.: US 7,684,537 B2
(45) Date of Patent: Mar. 23, 2010

(54) X-RAY CT APPARATUS

(75) Inventors: Yasuhiro Imai, Tokyo (JP); Motoki Watanabe, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 12/107,605

(22) Filed: Apr. 22, 2008

(65) Prior Publication Data
US 2008/0317196 A1    Dec. 25, 2008

(30) Foreign Application Priority Data
Apr. 23, 2007    (JP)    ............... 2007-112452

(51) Int. Cl.
*A61B 6/00*    (2006.01)
(52) U.S. Cl. .................... 378/8; 378/5; 378/16
(58) Field of Classification Search .............. 378/5, 378/8, 4, 15, 16
See application file for complete search history.

(56) References Cited

U.S. PATENT DOCUMENTS

| | | | |
|---|---|---|---|
| 5,751,782 A | 5/1998 | Yoshitome | |
| 6,275,560 B1 | 8/2001 | Blake et al. | |
| 6,510,337 B1 | 1/2003 | Heuscher et al. | |
| 6,560,309 B1 | 5/2003 | Becker et al. | |
| 6,721,386 B2 | 4/2004 | Bulkes et al. | |
| 6,836,529 B2 | 12/2004 | Li et al. | |
| 7,251,308 B2 | 7/2007 | Tsuyuki | |
| 7,313,213 B1 | 12/2007 | Hsieh et al. | |
| 2007/0041490 A1* | 2/2007 | Jha et al. | ......... 378/8 |

FOREIGN PATENT DOCUMENTS

| | | |
|---|---|---|
| JP | 2003-164446 | 6/2003 |
| JP | 2006-006531 | 1/2006 |

* cited by examiner

*Primary Examiner*—Hoon Song
(74) *Attorney, Agent, or Firm*—Armstrong Teasdale LLP

(57) ABSTRACT

In X-ray CT imaging for scanning a subject in the same anatomical region with two kinds of X-rays having different energy distributions, for the purpose of reducing a subject's positional offset between two kinds of tomographic images representing the same slice by a simple control scheme while reducing stress on the subject, a cardiac cycle identifying section 30*b* identifies a cardiac cycle of a subject 6 by an electrocardiograph 5 or the like, and a scan start time interval setting section 30*c* sets a time interval from the start of a first scan with first X-rays to the start of a second scan with second X-rays to a time approximately the same as the aforementioned cardiac cycle. A scan control section 30*a* controls several sections to keep a constant rotation speed of a rotating section 27 and start the scans at the aforementioned time interval. In each scan, projection data over a given view angle sufficient for reconstruction processing for a tomographic image are collected at once.

20 Claims, 15 Drawing Sheets

X-RAY CT APPARATUS

CROSS REFERENCE TO RELATED APPLICATIONS

This application claims the benefit of Japanese Patent Application No. 2007-112452 filed Apr. 23, 2007.

BACKGROUND OF THE INVENTION

The subject matter disclosed herein relates to an X-ray CT (Computed Tomography) apparatus, and particularly to an X-ray CT apparatus for performing X-ray CT imaging on the same anatomical region in a subject with a plurality of kinds of X-rays having different energy distributions to obtain a plurality of kinds of tomographic images representing the same slice but having different image properties.

Conventionally, there is a known X-ray CT imaging method comprising performing X-ray CT imaging on the same anatomical region in a subject with two kinds of X-rays having energy distributions different from each other to obtain two kinds of tomographic images representing the same slice but having image properties different from each other, and performing inter-image computational processing using the two kinds of tomographic images to obtain an enhanced image in which a difference between the tomographic images is enhanced (see Patent Document 1, for example).

In general, different kinds of substances have different X-ray energy absorption distributions, and when a subject is imaged with two kinds of X-rays having different energy distributions, the tomographic images of the subject obtained from the imaging operations have image properties, for example, contrasts, different from each other. Therefore, by focusing upon such a difference between the tomographic images, an image representing only a given substance or tissue can be extracted to aid in interpretation of tomographic images.

When imaging a subject with two kinds of X-rays to obtain such an enhanced image, a time difference occurs between the first and second imaging operations in principal, and a change in the position or posture of the subject between the first and second imaging operations causes a subject's positional offset between the two tomographic images. Such a positional offset causes incorporation of artifacts, in addition to a true difference due to the difference in image property between the tomographic images, into the enhanced image, thus interfering with proper observation or analysis of the enhanced image.

While it is possible to restrain subject's conscious action or respiration to some degree with the cooperation of the subject, a positional offset of the subject involved in, especially, subject's cardiac motion cannot be restricted. Thus, for example, when X-ray CT imaging is performed with an subject's artery taken as an anatomical region of interest, the position of the artery itself may vary with cardiac motion or the thickness of the artery may vary with a change of the blood flow rate, resulting in a positional offset of the anatomical region of interest among a plurality of kinds of tomographic images.

A method for solving such a problem that may be contemplated comprises applying an electrocardiological synchronized imaging technique. The electrocardiological synchronized imaging technique includes a prospective imaging method and a retrospective imaging method. The prospective imaging method comprises monitoring the subject's electrocardiographic waveform by an electrocardiograph, etc., and causing each scan to synchronize with a given cardiac phase after a given period of time from an R peak (see Japanese Patent Application Laid Open No. 2006-6531, for example). The retrospective imaging method comprises collecting projection data simultaneously with electrocardiographic waveform data of a subject, and extracting only the projection data corresponding to an arbitrary cardiac phase later in image reconstruction (see Japanese Patent Application Laid Open No. 2003-164446, for example). Since by applying such electrocardiological synchronized imaging techniques, reconstruction processing may be performed using projection data corresponding to a given cardiac phase zone in which subject's motion associated with cardiac motion is slow, the subject's positional offset due to cardiac motion among the resulting tomographic images can be suppressed.

SUMMARY OF THE INVENTION

When applying the prospective imaging method, however, a scan has to be made in synchronization with a specific cardiac phase in which the motion of the heart is slow, and therefore, the subject's cardiac phase must be constantly checked by monitoring the subject's electrocardiographic waveform or the like to determine when to start a scan for each scan, thus complicating control of the X-ray CT apparatus. When applying the retrospective imaging method, the subject is exposed to X-rays continuously and over a long time, and the exposure dose to the subject is increased. Especially when the retrospective imaging method is combined with contrast imaging, the contrast agent injected into the subject flows relatively fast, so that the total dosage of the contrast agent, and hence, stress on the subject is further increased, thus making such an imaging method impractical.

The present invention has been made in view of such circumstances, and its object is to provide an X-ray CT apparatus for scanning a subject with a plurality of kinds of X-rays having energy distributions different from one another, in which a subject's positional offset can be reduced among a plurality of kinds of tomographic images representing the same slice obtained by the scans by a simple control scheme while reducing stress on the subject.

In its first aspect, the present invention provides an X-ray CT apparatus comprising: an X-ray data collecting system provided with an X-ray generating section for generating X-rays and an X-ray detecting section comprising a large number of X-ray detector elements one- or two-dimensionally arranged, facing each other across a cavity and provided rotatably around a given axis; an imaging table for carrying a subject placed thereon through said cavity along said given axis; and scan control device for controlling said X-ray data collecting system and said imaging table to sequentially perform first and second scans with switched X-rays generated by said X-ray generating section, said first scan collecting projection data at a given position in a direction of said given axis over a given view angle sufficient for reconstruction processing for a tomographic image with first X-rays having a first energy distribution, and said second scan collecting projection data over said given view angle with second X-rays having a second energy distribution different from said first energy distribution, wherein said apparatus further comprises: cardiac cycle identifying device for identifying a cardiac cycle of said subject prior to said first scan; and scan start time interval setting device for setting a time interval from the start of said first scan to the start of said second scan to a time approximately the same as said identified cardiac cycle, said scan control device controlling said X-ray data collecting system to start said first and second scans at said set time interval and perform each of said scans within one cardiac cycle while rotating said X-ray data collecting system in a constant cycle of rotation such that cardiac phase coverage for said first scan approximately matches that for said second scan.

In its second aspect, the present invention provides the X-ray CT apparatus of the first aspect, wherein: said given view angle is an angle of 180° plus a fan angle of said X-rays; said apparatus further comprises cycle-of-rotation setting device for setting a cycle of rotation of said X-ray data collecting system to a given cycle approximately the same as said identified cardiac cycle; and said scan control device controls said X-ray data collecting system to rotate in said set cycle of rotation.

In its third aspect, the present invention provides the X-ray CT apparatus in the first aspect, wherein: said given view angle is 360°; said apparatus further comprises cycle-of-rotation setting device for setting a cycle of rotation of said X-ray data collecting system to a given cycle approximately the same as a cycle determined by subtracting a time required to switch said X-rays from said identified cardiac cycle; and said scan control device controls said X-ray data collecting system to rotate in said set cycle of rotation.

In its fourth aspect, the present invention provides the X-ray CT apparatus in the second or third aspect, wherein: said scan control device controls said X-ray data collecting system and said imaging table to sequentially move said given position to a plurality of positions arranged in a direction of said given axis, and perform said first and second scans at each of said positions.

In its fifth aspect, the present invention provides the X-ray CT apparatus in the fourth aspect, wherein: said scan control device controls said X-ray data collecting system to perform said first and second scans at said plurality of positions all at the same said time interval and in the same said cycle of rotation.

In its sixth aspect, the present invention provides the X-ray CT apparatus in the fourth aspect, wherein: said cardiac cycle identifying device identifies a cardiac cycle of said subject each time said given position is moved; said scan start time interval setting device sets said time interval to a time approximately the same as said identified cardiac cycle each time said given position is moved; and said cycle-of-rotation setting device sets said cycle of rotation to said given cycle based on said cardiac cycle each time said given position is moved.

In its seventh aspect, the present invention provides the X-ray CT apparatus in the sixth aspect, wherein: said cardiac cycle identifying device identifies a cardiac cycle of said subject while said given position is being moved to a next position; said cycle-of-rotation setting device sets said given cycle based on said identified cardiac cycle while said given position is being moved to a next position; and said scan control device starts control of said X-ray data collecting system to bring said cycle of rotation close to said set given cycle while said given position is being moved to a next position.

In its eighth aspect, the present invention provides the X-ray CT apparatus in any one of the fourth through seventh aspects wherein: said scan control device controls said X-ray data collecting system to match the angular position of said X-ray data collecting system at the start of said first scan all to the same angular position at said plurality of positions.

In its ninth aspect, the present invention provides the X-ray CT apparatus in the first aspect, wherein: said scan control device controls said X-ray data collecting system and said imaging table to sequentially move said given position to a plurality of positions arranged in a direction of said given axis, and perform said first and second scans at each of said positions.

In its tenth aspect, the present invention provides the X-ray CT apparatus in the ninth aspect, wherein: said scan control device controls said X-ray data collecting system to start said first and second scans all at the same said time interval at said plurality of positions.

In its eleventh aspect, the present invention provides the X-ray CT apparatus in the ninth aspect, wherein: said cardiac cycle identifying device identifies a cardiac cycle of said subject each time said given position is moved; and said scan start time interval setting device sets said time interval to a time approximately the same as said identified cardiac cycle each time said given position is moved.

In its twelfth aspect, the present invention provides the X-ray CT apparatus in any one of first through eleventh aspects, further comprising: image producing device for processing first projection data acquired by said first scan and second projection data acquired by said second scan to produce an enhanced image in which a difference between a tomographic image from said first projection data and a tomographic image from said second projection data representing mutually the same slice is enhanced.

In its thirteenth aspect, the present invention provides the X-ray CT apparatus in the twelfth aspect, wherein: said image producing device applies reconstruction processing to said first projection data to obtain a first tomographic image, applies reconstruction processing to said second projection data to obtain a second tomographic image, and performs inter-image computational processing between said first and second tomographic images to produce said enhanced image.

In its fourteenth aspect, the present invention provides the X-ray CT apparatus in the thirteenth aspect, wherein: said inter-image computational processing is addition/subtraction processing.

In its fifteenth aspect, the present invention provides the X-ray CT apparatus in any one of first through fourteenth aspects, wherein: said reconstruction processing is based on a backprojection technique.

In its sixteenth aspect, the present invention provides the X-ray CT apparatus in any one of first through fifteenth aspects, wherein: said cardiac cycle identifying device identifies a cardiac cycle based on signals acquired by an electrocardiograph, a heart rate monitor or a pulsemeter.

In its seventeenth aspect, the present invention provides the X-ray CT apparatus in any one of first through sixteenth aspects, wherein: said X-ray generating section comprises an X-ray tube, and said first X-rays and said second X-rays are those with mutually different tube voltages for said X-ray tube generating X-rays.

In its eighteenth aspect, the present invention provides the X-ray CT apparatus in any one of first through seventeenth aspects, wherein: said X-ray detecting section is a multi-row X-ray detecting section or an X-ray area detector in a matrix structure.

As used herein, the expression "carrying something through" implies "carrying something into" and "carrying something out of."

As used herein, by the phrase "at a given position" is meant "with a center of rotation of the X-ray data collecting system fixed at one position in a direction of a given axis.

As used herein, the term "energy distribution" refers to a distribution representing the relationship between the X-ray energy and the strength for that energy, an example of which may be a graph with a horizontal axis of the photon energy (keV), and a vertical axis of the number of photons.

As used herein, the phrase "setting a time interval from the start of said first scan to the start of said second scan to a time approximately the same as said identified cardiac cycle," or "setting a cycle of rotation of said X-ray data collecting system to a given cycle approximately the same as . . . " involves, when a time interval from the start of a first scan to the start of a second scan or a cycle of rotation of the X-ray data collecting system can be set only in a stepwise manner at a given step size, setting such a time interval or cycle of rotation with a lag of the order of the step size; for example, a lag up to about 0.05 sec. is allowable for a cycle of rotation that can be set at 0.05-sec. steps.

As used herein, the term "scan" refers to collection of projection data over a given view angle sufficient to reconstruct one tomographic image; for example, a half scan in which 180° plus an X-ray fan angle α of projection data are collected or a full scan in which 360° of projection data are collected may be contemplated.

As used herein, the term "X-ray fan angle" refers to an angle of X-ray emission with respect to a rotation angle direction of the X-ray data collecting system, i.e., a channel direction of the X-ray detecting section.

As used herein, the term "time required to switch X-rays" refers to a time required for the X-ray source to shift to an X-ray generatable state with a given intended energy distribution; for example, when the X-ray source comprises an X-ray tube, the term may refer to a time required for the tube voltage for the X-ray tube to reach a specific intended range. Particularly, the "required time" may be about 0.2 sec., for example.

The substances extractable based on a "difference" may include, for example, given substances such as fat, calcium, etc.; soft tissue such as brain or organs; bone tissue such as ribs or spine; and given tissue in a specific anatomical region having CT values falling within a specific range.

The "enhanced images" may include, for example, various material decomposition images such as a soft portion image in which soft tissue is enhanced, a bone image in which bone tissue is enhanced, a fat distribution image in which fat is enhanced, and a calcium distribution image in which calcium is enhanced.

The "image producing device" may be, for example, device of obtaining enhanced image data by performing reconstruction processing after inter-image computational processing between the first and second projection data.

The "addition/subtraction processing" may include processing of simple addition or subtraction on raw data, and in addition, processing of addition or subtraction after weighting or shifting data at least on the one hand, and may include, for example, processing of subtraction after transforming all CT values in the whole data on the one hand so that CT values in the given anatomical regions corresponding to each other become equal.

The "backprojection technique" may include, for example, a convolution backprojection technique.

The "cardiac cycle identifying device" may include, for example, device of calculating a cardiac cycle by acquiring electrocardiographic waveform signals or electrocardiological synchronization signals that represents heart beat synchronization signals from an electrocardiograph, or by acquiring heart beat synchronization signals from a heart rate monitor or a pulsemeter, and device of acquiring information representing a cardiac cycle from an electrocardiograph, a heart rate monitor or a pulsemeter. When the "cardiac cycle identifying device" is of a type that acquires heart beat synchronization signals to calculate a cardiac cycle, it may calculate a cardiac cycle as the time between two consecutive heart beat synchronization signals, or as the time obtained by calculating the time between two consecutive heart beat synchronization signals in three or more consecutive heart beat synchronization signals for each combination of the two consecutive heart beat synchronization signals therein, and averaging the times between the signals in such combinations. If the latter is employed, and when the time between the signals represents an extremely long or short cardiac cycle as compared with the previously calculated cardiac cycle, that is, for example, when the time between the signals represents a cardiac cycle 20% longer or shorter than the previously calculated cardiac cycle, the time between the signals is desirably unused in calculating a new cardiac cycle. Thus, even if the heart beat becomes out of order due to, for example, arrhythmia of the subject, the calculated cardiac cycle can be prevented from extreme variation, thus enabling identification of a more substantial cardiac cycle. Moreover, the "cardiac cycle identifying device" may calculate a cardiac cycle by counting the number of heart beat synchronization signals within a given period of time, and dividing the given period of time by the counted number of heart beat synchronization signals.

It should be noted that the "cardiac cycle identifying device" that merely identifies at least a cardiac cycle may be sufficient, and the device needs not identify the cardiac phase of the subject in real time.

The "heart rate monitor" or "pulsemeter" may include, for example, an instrument for detecting body motion of the torso, arm, finger or the like, and outputting heart beat synchronization signals or information representing a cardiac cycle.

The "subject" may include animal patients in addition to human patients.

According to the X-ray CT apparatus of the present invention, a subject's cardiac cycle is identified by the cardiac cycle identifying device prior to a first scan; a time interval from the start of a first scan to the start of a second scan is set by the scan start time interval setting device to a time approximately the same as the aforementioned identified cardiac cycle; and the X-ray data collecting system is controlled by the scan control device to start the first and second scans at the set time interval and perform each of the scans within one cardiac cycle while rotating the X-ray data collecting system in a constant cycle of rotation such that cardiac phase coverage for the first scan approximately matches that for the second scan. Therefore, two kinds of projection data can be collected by only two consecutive scans, in which data temporal changes involved in subject's cardiac motion during the scans are approximately the same as each other, that is, in which data the aforementioned subject's temporal change appears as distortion approximately the same as each other on reconstructed tomographic images, but does not appear as a difference between tomographic images. Thus, in an X-ray CT apparatus for scanning a subject with a plurality of kinds of X-rays having different energy distributions, it is possible to reduce a subject's positional offset among a plurality of kinds of tomographic images representing the same slice obtained by the scans by a simple control scheme while reducing stress on the subject.

DETAILED DESCRIPTION OF THE INVENTION

Now embodiments of the present invention will be described with reference to the accompanying drawings.

An X-ray CT apparatus in accordance with one embodiment of the present invention will be described.

Figure 1:
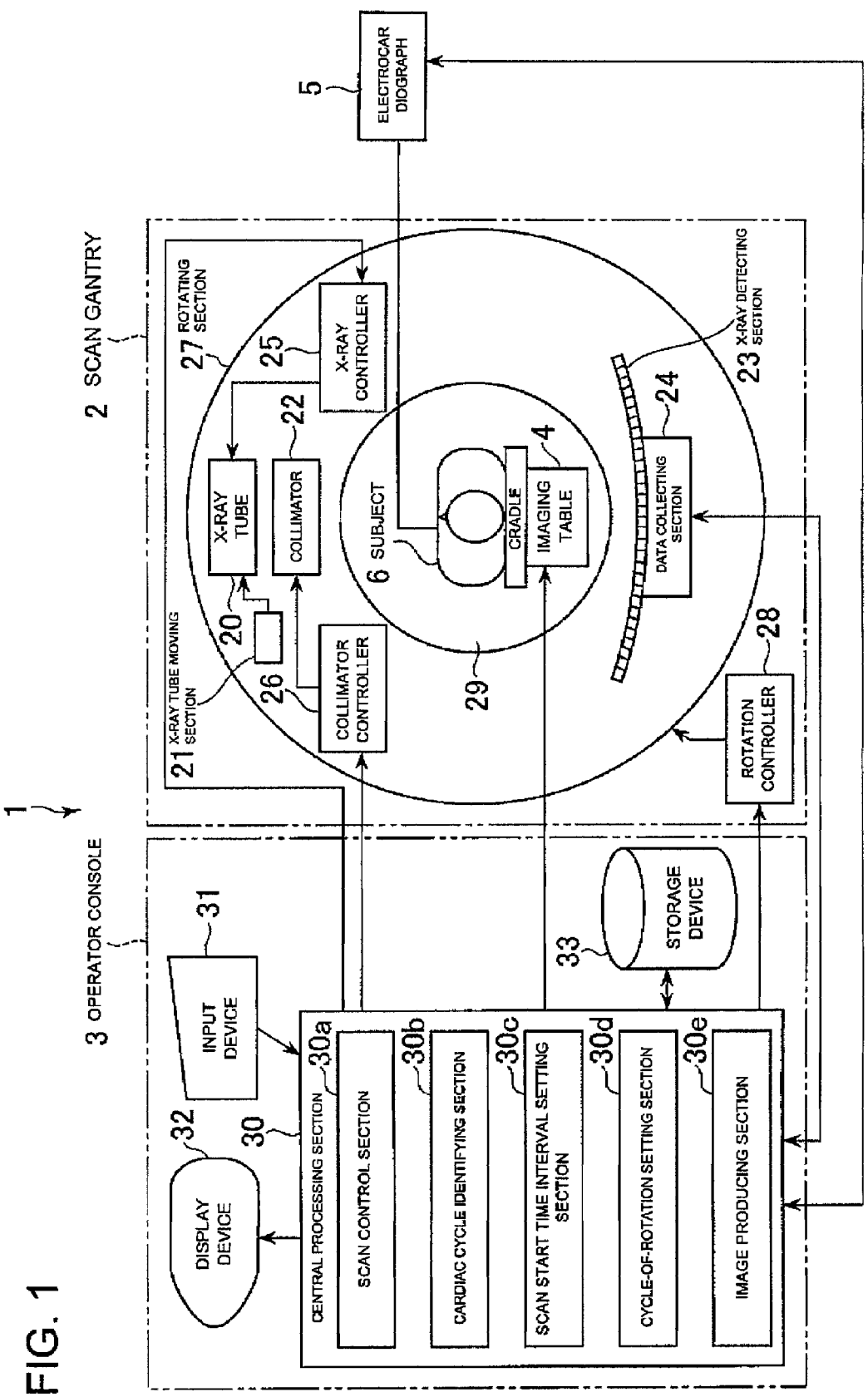
FIG. 1 is a diagram showing a configuration of an X-ray CT apparatus in accordance with one embodiment of the present invention.

FIG. 1 is a block diagram showing an overall configuration of an X-ray CT apparatus 1 of the present embodiment. As shown in FIG. 1, the X-ray CT apparatus 1 of the present embodiment comprises a scan gantry 2, an operator console 3, and an imaging table 4.

The scan gantry 2 comprises an X-ray tube 20, an X-ray tube moving section 21, a collimator 22, an X-ray detecting section 23, a data collecting section 24, an X-ray controller 25, a collimator controller 26, a rotating section 27, and a rotation controller 28. The scan gantry 2 has therein a bore 29 through which the subject 6 is carried, and the X-ray tube 20 and X-ray detecting section 23 are disposed to face each other across the bore 29.

The X-ray tube 20 is provided for emitting X-rays. In the present embodiment, the X-ray tube 20 emits X-rays toward the subject 6 carried into the bore 29 based on a control signal from the X-ray controller 25. The X-ray tube 20 emits first X-rays having a first energy distribution at a first tube voltage, and emits second X-rays having a second energy distribution at a second tube voltage different from the first tube voltage.

The X-ray tube moving section 21 moves a center of emission from the X-ray tube 20 in a slice thickness direction z for the subject 6 placed on the imaging table 4 in the bore 29 of the scan gantry 2 based on a control signal from the X-ray controller 25.

The collimator 22 is disposed between the X-ray tube 20 and X-ray detecting section 23. The collimator 22 is made from, for example, two plates provided in a channel direction x and two plates provided in the slice thickness direction z. The collimator 22 moves the two plates provided in each direction independently based on a control signal from the collimator controller 26 to intercept the X-rays emitted from the X-ray tube 20 in that direction to form them into a cone-like shape, thus regulating the coverage of X-ray emission.

The X-ray detecting section 23 is disposed to face the X-ray tube 20 across the bore 29. The X-ray detecting section 23 detects X-rays emitted by the X-ray tube 20 in a plurality of view directions around the subject 6 and passing through the subject 6 to generate projection data for each view direction.

Figure 2:
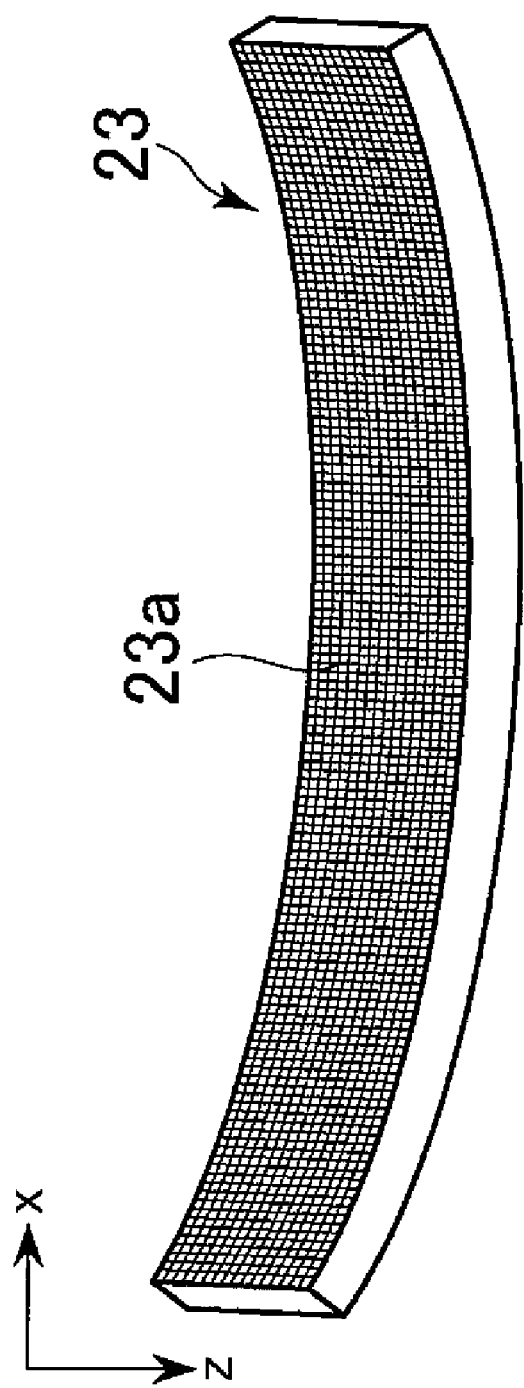
FIG. 2 is a diagram showing a configuration of an X-ray detecting section in accordance with one embodiment of the present invention.

FIG. 2 is a perspective view showing a configuration of the X-ray detecting section 23. As shown in FIG. 2, the X-ray detecting section 23 has X-ray detector elements 23a for detecting X-rays two-dimensionally arranged in an array in the channel direction x and slice thickness direction z. Specifically, the X-ray detecting section 23 has X-ray detector elements 23a two-dimensionally arranged in an array in the channel direction x and slice thickness direction z, the channel direction x being along a rotation angle direction for the X-ray tube 20 rotated by the rotating section 27 around a straight line parallel to the body axis direction or carrying direction for the subject 6, and the slice thickness direction z being a direction generally perpendicular to a plane formed by a trajectory drawn by the rotation of the X-ray tube 20 by the rotating section 27. The two-dimensionally arranged plurality of X-ray detector elements 23a together form a plane of X-ray impingement curved in the form of a cylindrical concave surface. In such a configuration, 1,000 X-ray detector elements 23a, for example, are arranged in the channel direction x, and eight X-ray detector elements 23a, for example, are arranged in the slice thickness direction z. While the X-ray detecting section 23 desirably is such a multi-row X-ray detector or X-ray area detector in a matrix structure, it may be a single-row X-ray detector.

The X-ray detector elements 23a comprise a scintillator (not shown), for example, for converting the detected X-rays into light, and photodiodes (not shown) for converting the light converted by the scintillator into an electrical charge, so that the X-ray detecting section 23 is constructed as a solid state detector. It should be noted that the X-ray detector elements 23a are not limited thereto, and may be, for example, semiconductor detector elements employing cadmium-tellurium (CdTe) or the like, or of an ionization-chamber type using a xenon (Xe) gas.

Figure 3:
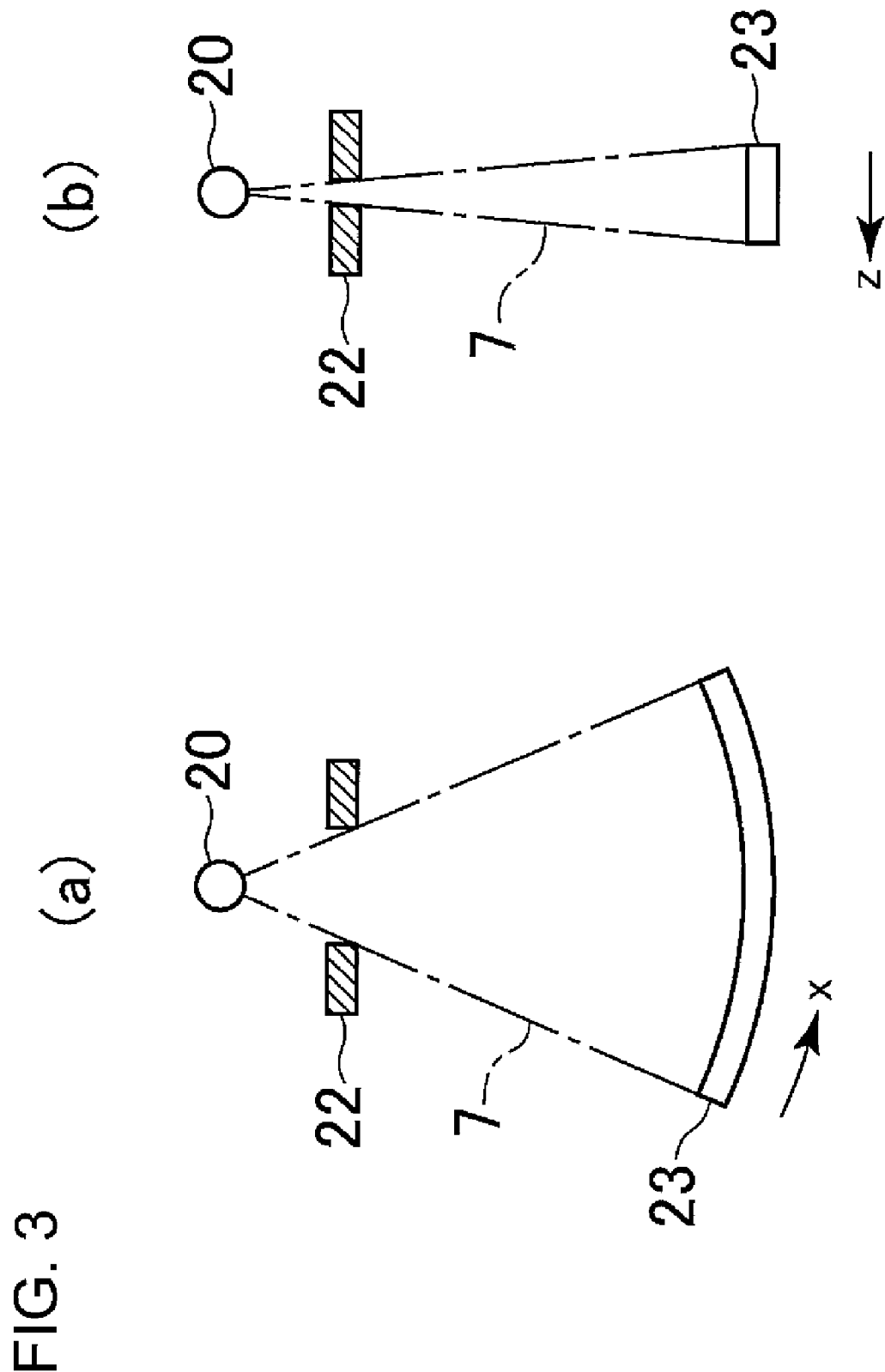
FIGS. 3(a) and 3(b) are diagrams showing a mutual relationship among an X-ray tube, a collimator, and an X-ray detecting section in accordance with one embodiment of the present invention.
Figure 4:
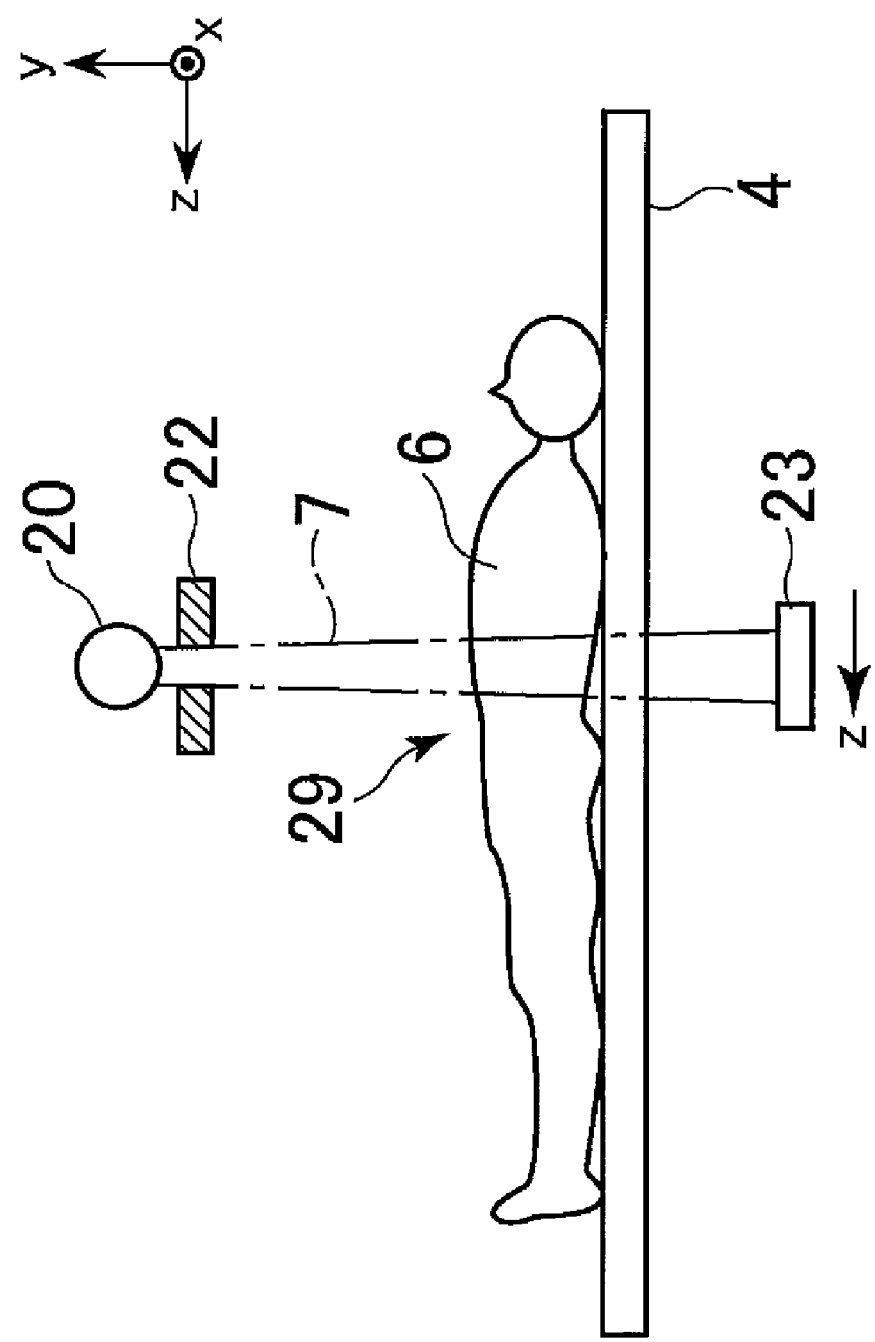
FIG. 4 is a diagram showing a mutual relationship among an X-ray tube, a collimator, and an X-ray detecting section in accordance with one embodiment of the present invention.

FIGS. 3(a), 3(b), and 4 are diagrams showing the mutual relationship among the X-ray tube 20, collimator 22 and X-ray detecting section 23. FIG. 3(a) is a diagram as viewed in the slice thickness direction z, and FIG. 3(b) is a diagram as viewed in the channel direction x. FIG. 4 shows imaging on the subject 6 as viewed in the channel direction x, as in FIG. 3(b).

As shown in FIGS. 3(a) and 3(b), the X-rays 7 emitted from the X-ray tube 20 are formed into a cone-like shape by the collimator 22, and cast onto the X-ray detecting section 23. In imaging the subject 6, the subject 6 is laid on the imaging table 4, and the subject 6 thus laid is carried into the bore 29. As shown in FIG. 4, the X-rays 7 are then emitted in a plurality of view directions from the circumference around the subject 6 around a straight line in the slice thickness direction z of the subject 6, and X-rays passing through the subject 6 through the collimator 22 are detected by the X-ray detecting section 23 for each view direction to generate projection data for the subject 6.

The data collecting section 24 collects the projection data detected and generated by the X-ray detecting section 23, and outputs them to the operator console 3. The data collecting section 24 comprises, for example, selection/addition switching circuit (not shown), and an analog-to-digital converter (not shown). In response to a control signal from the operator console 3, the selection/addition switching circuit selects projection data and adds them in a varying combination, and outputs the resulting data to the analog-to-digital converter. The projection data selected or added in a varying combination by the selection/addition switching circuit are converted from an analog signal to a digital signal by the analog-to-digital converter and output to the operator console 3.

The X-ray controller 25 outputs a control signal to the X-ray tube 20 to control the X-ray tube 20, in response to a control signal from the operator console 3. The X-ray controller 25 also outputs a control signal to the X-ray tube moving section 21 to make control so that the center of emission from the X-ray tube 20 is moved in the slice thickness direction z, in response to a control signal from the operator console 3.

The collimator controller 26 outputs a control signal to the collimator 22 for controlling the collimator 22 to shape X-rays emitted from the X-ray tube 20, in response to a control signal from the operator console 3.

The rotating section 27 rotates around an iso-center of the bore 29 in response to a control signal from the rotation controller 28. The rotating section 27 is provided with the X-ray tube 20, X-ray tube moving section 21, collimator 22, X-ray detecting section 23, data collecting section 24, X-ray controller 25, and collimator controller 26, which are changed in position relative to the subject 6 carried into the bore 29 with rotation of the rotating section 27. By rotating the rotating section 27, X-rays are emitted in a plurality of view directions around a straight line in the slice thickness direction z of the subject 6, and X-rays passing through the subject are detected.

The rotation controller 28 outputs a control signal to the rotating section 27 for controlling the rotating section 27 to rotate, in response to a control signal from the operator console 3.

The operator console 3 comprises a central processing apparatus 30, an input device 31, a display device 32, and a storage device 33.

The central processing apparatus 30 is comprised of, for example, a computer, and has a scan control section 30a, a cardiac cycle identifying section 30b, a scan start time interval setting section 30c, a cycle-of-rotation setting section 30d, and an image producing section 30e.

The scan control section 30a controls several sections to perform a scan based on scan conditions input via the input device 31, in which scan X-rays are emitted from the X-ray tube 20 toward the subject 6 and X-rays passing through the subject 6 are detected by the X-ray detecting section 23. More particularly, the scan control section 30a controls the rotating section 27 and imaging table 4 to sequentially move a given position to be scanned to a plurality of positions lined up in the z direction, and at each of the positions, sequentially perform a first scan using first X-rays at a first tube voltage, and a second scan using second X-rays at a second tube voltage different from the first tube voltage with switched X-rays generated at the X-ray tube 20, and collect first projection data corresponding to the first scan and second projection data corresponding to the second scan. Both the first and second projection data are projection data for a plurality of views over a given view angle sufficient for reconstruction processing for a tomographic image, i.e., those required to reconstruct one tomographic image. The given view angle may be, for example, 180° plus an X-ray fan angle $\alpha$ for a half scan, and 360° for a full scan. Both the first and second projection data are projection data that can be acquired in one scan, i.e., projection data that are acquired by emitting X-rays toward the subject 6 while the rotating section 27 rotates over the aforementioned given view angle.

In particular, the scan control section 30a outputs a control signal to the imaging table 4 based on the scan conditions to carry the imaging table 4 into the bore 29 of the scan gantry 2 and control the position at which the subject 6 is scanned. The scan control section 30a also outputs a control signal to the rotation controller 28 to rotate the rotating section 27 of the scan gantry 2 and control a cycle of rotation of the rotating section 27. Moreover, the scan control section 30a outputs a control signal to the X-ray controller 25 to control the tube voltage for the X-ray tube 20 and the time at which X-rays are emitted. The scan control section 30a also outputs a control signal to the collimator controller 26 for controlling the collimator 22 to shape X-rays. Furthermore, the scan control section 30a outputs a control signal to the data collecting section 24 for making control to collect projection data acquired by the X-ray detector elements 23a in the X-ray detecting section 23.

The cardiac cycle identifying section 30b identifies a cardiac cycle of the subject 6 prior to a first scan, by acquiring electrocardiological synchronization signals from the electrocardiograph 5 connected to the subject 6 and calculating a cardiac cycle.

The scan start time interval setting section 30c sets, based on the cardiac cycle identified by the cardiac cycle identifying section 30b, a time interval from the start of a first scan to the start of a second scan to a time approximately the same as the identified cardiac cycle.

The cycle-of-rotation setting section 30d sets the cycle of rotation of the rotating section 27 to a given cycle based on the identified cardiac cycle, based on the cardiac cycle identified by the cardiac cycle identifying section 30b. The given cycle may be, for example, a cycle approximately the same as the identified cardiac cycle for a half scan, and a cycle determined by subtracting the time required to switch X-rays from the identified cardiac cycle for a full scan. As used herein, the time required to switch X-rays refers to a time required to switch X-rays to be emitted from the first X-rays to the second X-rays, or from the second X-rays to the first X-rays, which time is principally constituted by the time required to change the tube voltage.

Thus, the scan control section 30a outputs a control signal to the rotation controller 28 to rotate the rotating section 27 in a cycle of rotation set by the cycle-of-rotation setting section 30d, and outputs a control signal to the X-ray controller 25 and data collecting section 24 to sequentially perform first and second scans at a time interval set by the scan start time interval setting section 30c. It should be noted that the scan control section 30a performs the scans at the aforementioned plurality of positions all at the same time interval and in the same cycle of rotation.

The image producing section 30e processes the first and second projection data acquired by the X-ray detecting section 23 to produce an enhanced image in which a difference between a tomographic image by the first projection data and a tomographic image by the second projection data representing mutually the same slice is enhanced. In the present embodiment, the image producing section 30e first applies reconstruction processing to the first projection data according to a known reconstruction technique such as, for example, a convolution backprojection technique to obtain a first tomographic image of the subject 6, and applies reconstruction processing to the second projection data to obtain a second tomographic image of the subject 6. In other words, the image producing section 30e applies reconstruction processing to the first and second projection data corresponding to approximately the same cardiac phase coverage to produce a first tomographic image at a first tube voltage and a second tomographic image at a second tube voltage in the scanned cardiac phase coverage and at the scanned position approximately the same as each other. Thereafter, the image producing section 30e performs inter-image computational processing between the first and second tomographic images to produce an enhanced image in which a difference between the two tomographic images is enhanced, wherein the inter-image computational processing is weighted subtraction processing, and the enhanced image produced is an image in which soft tissue of the subject 6 is principally enhanced or that in which bone tissue of the subject 6 is principally enhanced.

It should be noted that the weighted subtraction processing refers to processing of applying transformation processing to CT values in at least one tomographic image such that a sub-image corresponding to given tissue in one tomographic image has CT values equal to those of a sub-image corresponding to the same given tissue in the other tomographic image, and then performing subtraction processing between the tomographic images to produce an image in which the sub-image corresponding to given tissue is removed to enhance the presence of the other. Moreover, the image producing section 30e is connected to the storage device 33 for storing therein the produced enhanced image of the subject 6.

The input device 31 in the operator console 3 is comprised of input devices such as, for example, a keyboard and a mouse. The input device 31 is provided for supplying to the central processing apparatus 30 several kinds of information such as, for example, imaging conditions including actual scan conditions, and information on the subject 6.

The display device 32 is comprised of, for example, a CRT (cathode ray tube). The display device 32 displays the enhanced image of the subject 6 produced by the image producing section 30e and several other kinds of information based on instructions from the central processing apparatus 30.

The storage device 33 is comprised of a memory for storing several kinds of data including images produced by the image producing section 30e, programs and the like. The storage device 33 is accessed by the central processing apparatus 30 for the stored data as needed.

The imaging table 4 is comprised of a table for laying thereon the subject 6 that is an object to be imaged. The imaging table 4 carries the subject 6 into the bore 29 in the scan gantry 2 based on a control signal from the operator console 3. Moreover, the imaging table 4 moves the scanned position to each of the aforementioned positions.

The electrocardiograph 5 calculates a cardiac cycle based on an interval between R-peaks in a measured electrocardiographic waveform for the subject 6, and outputs information representing the cardiac cycle to the cardiac cycle identifying section 30b.

It should be noted that the X-ray tube 20 is an example of the X-ray generating section in the present invention. The rotating section 27 is an example of the X-ray data collecting system in the present invention.

Now an X-ray CT imaging method using the X-ray CT apparatus 1 in accordance with the present embodiment will be described.

Figure 5:
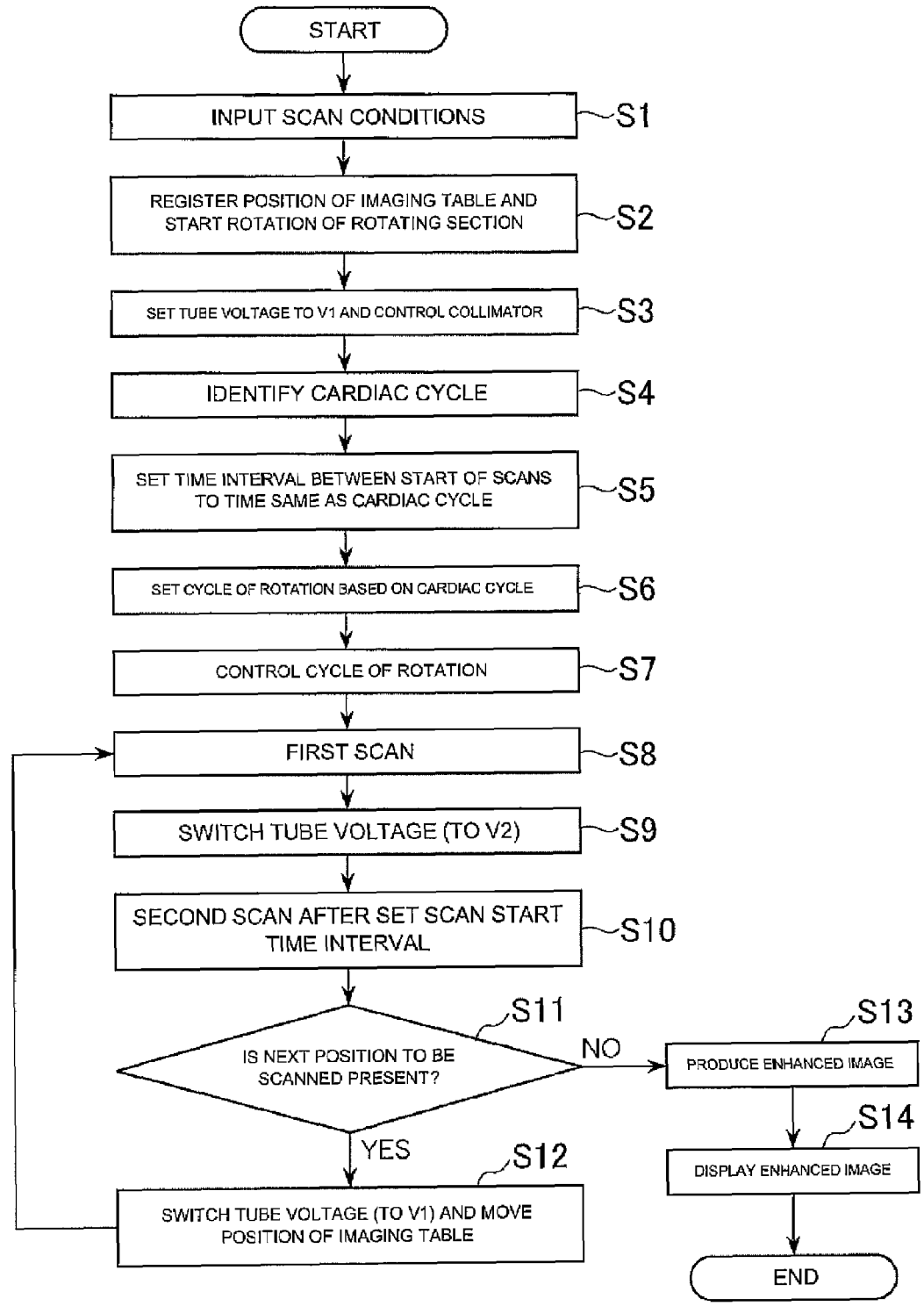
FIG. 5 is a flow chart showing an X-ray CT imaging method using an X-ray CT apparatus in accordance with one embodiment of the present invention.
Figure 6:
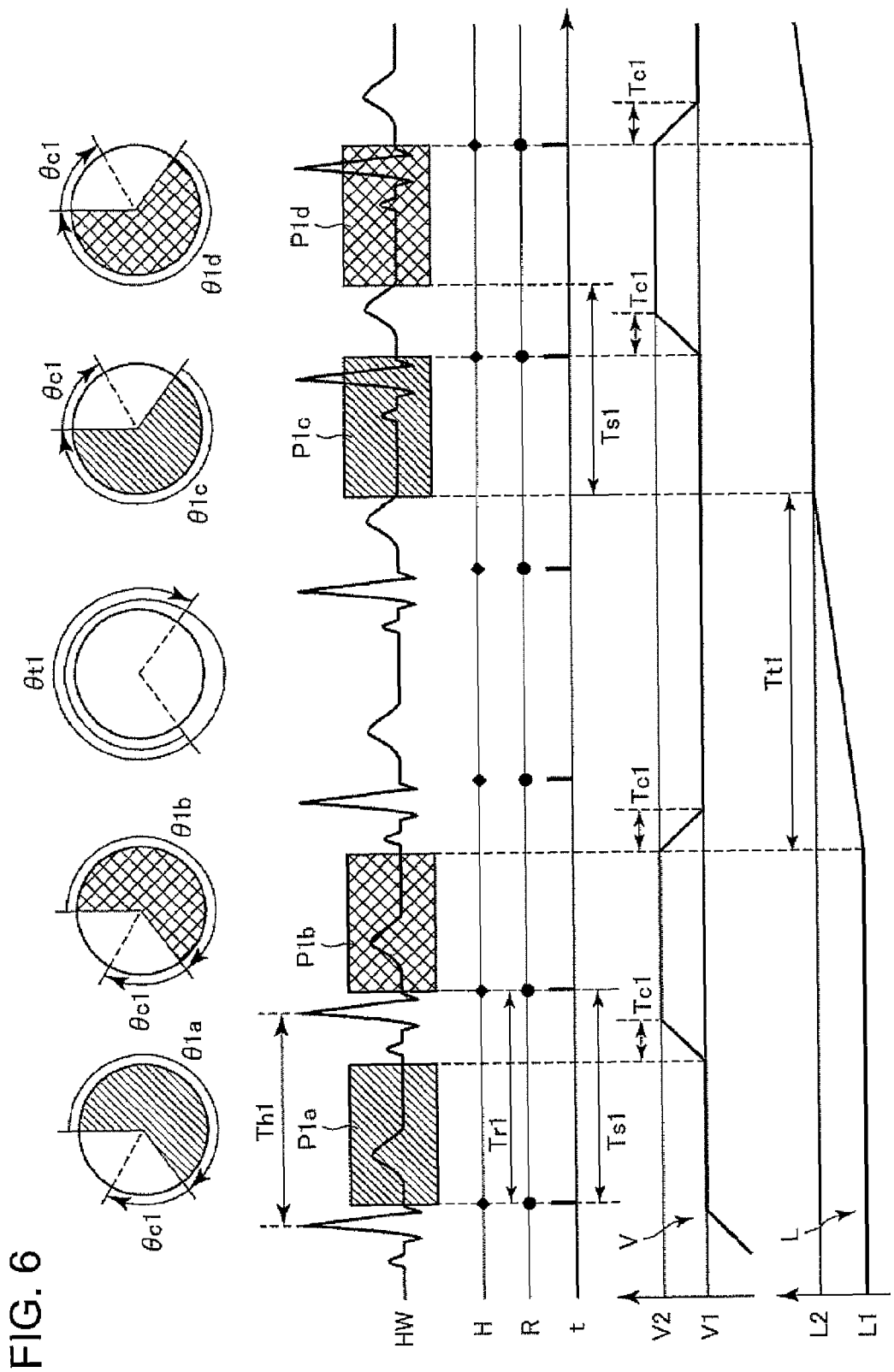
FIG. 6 is a drawing showing a time chart of scan processing in a half scan mode in accordance with one embodiment of the present invention.
Figure 7:
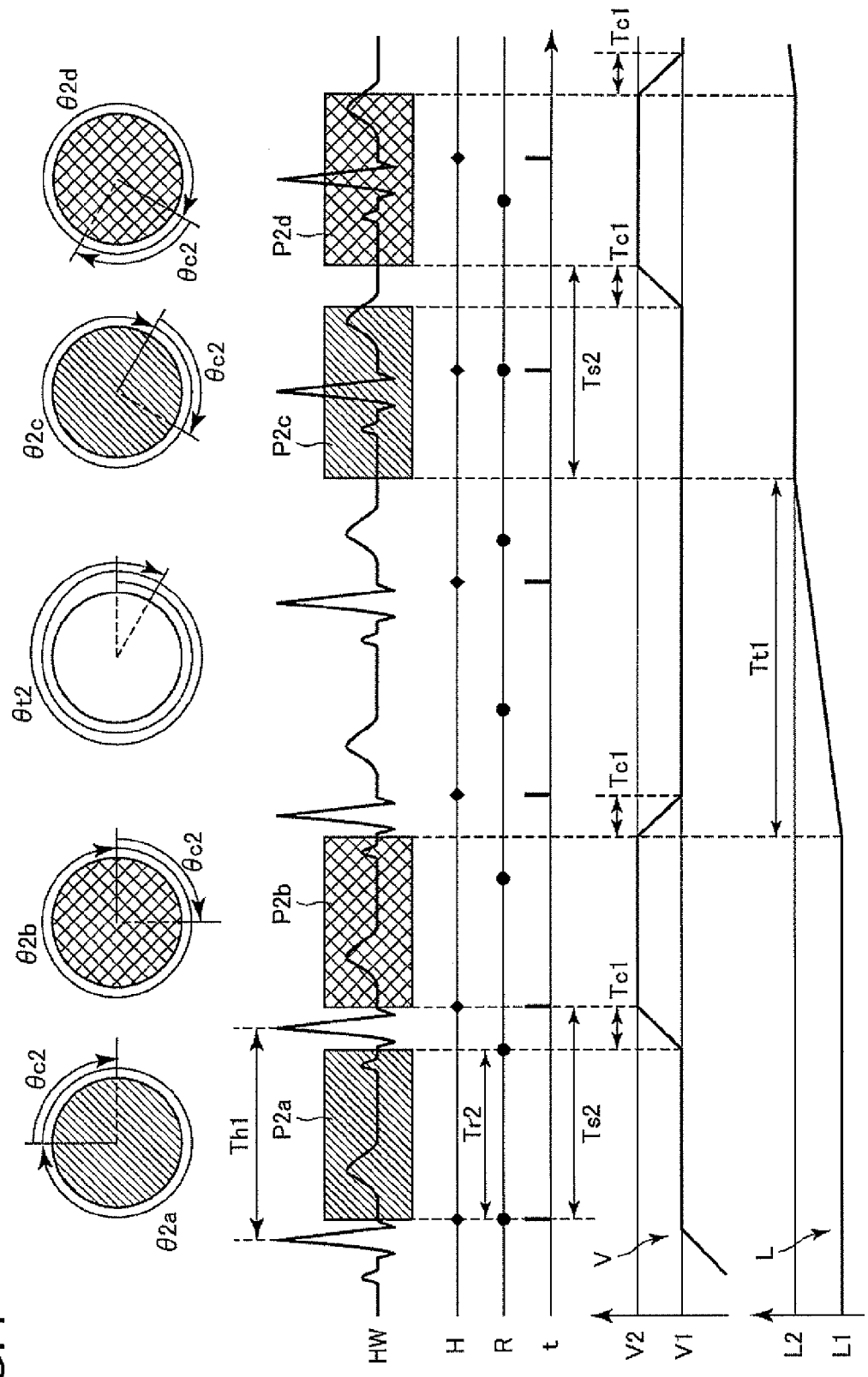
FIG. 7 is a drawing showing a time chart of scan processing in a full scan mode in accordance with one embodiment of the present invention.

FIG. 5 is a flow chart showing an X-ray CT imaging method using the X-ray CT apparatus in accordance with the present embodiment. FIGS. 6 and 7 are drawings showing time charts of scan processing in accordance with the present embodiment, in which FIG. 6 represents a scan mode being a half scan mode, and FIG. 7 represents a scan mode being a full scan mode. In FIGS. 6 and 7, there are shown a relative time t with reference to the start time of a first scan, a cardiac phase H of the subject 6, an electrocardiographic waveform HW for the subject 6, a rotation phase R of the rotating section 27, a tube voltage V for the X-ray tube 20, a position L of the imaging table 4, a time P at which projection data is collected, and a rotation angle θ of the rotating section 27.

First, a human operator inputs several setting particulars of actual scan conditions into the input device 31, which are output to the central processing apparatus 30 (S1). For example, the actual scan conditions including a section to be imaged, a slice thickness, a number of slices, a first tube voltage V1 and a second tube voltage V2, a scan mode representing half scan or full scan, an imaging scheme representing axial scan or helical scan, are input to the input device 31 by the operator. The section to be imaged is determined based on a scout image of the subject 6 acquired in a scout scan performed beforehand. The tube voltage V may be, for example, 80 kV for the first tube voltage V1, and 120 kV for the second tube voltage V2.

The scan control section 30a in the central processing apparatus 30 outputs a control signal to the scan gantry 2 and imaging table 4 to carry the imaging table 4 into or out of the bore 29 in the scan gantry 2 to register the position of the imaging table 4 to a position L1 for an initial scan, and at the same time, start rotation of the rotating section 27 of the scan gantry 2 (S2).

The scan control section 30a outputs a control signal to the X-ray controller 25 and collimator controller 26 to set the tube voltage V for the X-ray tube 20 to a first tube voltage V1, and at the same time, control the collimator 22 to appropriately shape X-rays from the X-ray tube 20 (S3).

The cardiac cycle identifying section 30b identifies a cardiac cycle Th of the subject 6 based on information representing a cardiac cycle acquired from the electrocardiograph 5 (S4).

The scan start time interval setting section 30c sets the time interval Ts from the start of a first scan at the first tube voltage V1 to the start of a second scan at the second tube voltage V2 to a time Ts1 that is the same as the identified cardiac cycle Th1 (S5). Moreover, the cycle-of-rotation setting section 30d sets the cycle of rotation Tr of the rotating section 27 to a given cycle Tr1 that is the same as the identified cardiac cycle Th1 when the scan mode is in a half scan mode, or sets the cycle of rotation Tr of the rotating section 27 to a given cycle Tr2 determined by subtracting the time Tc1 required to switch X-rays from the identified cardiac cycle Th1 when the scan mode is in a full scan mode (S6). At that time, if the cycle of rotation Tr of the rotating section 27 can be set only at a given step size, the cycle of rotation is set to a value closest to the aforementioned given cycle among settable ones.

For example, when the cardiac cycle Th1=1.0 sec. (heart rate=60/minute) and the time required to switch X-rays Tc1=0.2 sec., setting is made such that the time interval between the start of scans Ts1=1.0 sec. and the cycle of rotation Tr1=1.0 sec. for a half scan, and the time interval between the start of scans Ts2=1.0 sec. and the cycle of rotation Tr2=1.0−0.2=0.8 sec. for a full scan. Moreover, for example, when the cardiac cycle Th1=0.6 sec. (heart rate=100/minute), and the time required to switch X-rays Tc1=0.2 sec., setting is made such that the time interval between the start of scans Ts1=0.6 sec. and the cycle of rotation Tr1=0.6 sec. for a half scan, and the time interval between the start of scans Ts2=0.6 sec. and the cycle of rotation Tr2=0.6−0.2=0.4 sec. for a full scan.

The scan control section 30a outputs a control signal to the rotation controller 28 to control rotation such that the cycle of rotation of the rotating section 27 becomes a cycle set by the cycle-of-rotation setting section 30d (S7).

Once preparation has been all made, the scan control section 30a outputs a control signal to the X-ray controller 25 and data collecting section 24 to perform a first scan in which X-rays are emitted from the X-ray tube 20 over a given period of time and projection data generated at the X-ray detecting section 22 are collected (S8). At that time, projection data P1a for a plurality of views in a view angle range of θ1a corresponding to a view angle of 180° plus an X-ray fan angle α are collected as first projection data in a half scan mode, and projection data P2a for a plurality of views in a view angle range of θ2a corresponding to a view angle of 360° are collected as first projection data in a full scan mode.

After the first scan has been completed, the scan control section 30a outputs a control signal to the X-ray controller 25 to switch the tube voltage V for the X-ray tube 20 to a second tube voltage V2 (S9). During the switching of the tube voltage, the rotating section 27 rotates by a rotation angle equal to (the time required to switch the tube voltage×360°/the cycle of rotation). Specifically, it rotates by an angular range θc1 representing a rotation angle equal to (Tc1×360/Tr1) in a half scan mode, and by an angular range θc2 representing a rotation angle equal to (Tc1×360/Tr2) in a full scan mode.

The scan control section 30a then outputs a control signal to the X-ray controller 25 and data collecting section 24 to perform a second scan in which X-rays are emitted from the X-ray tube 20 over a given period of time and projection data generated at the X-ray detecting section 22 are collected (S10). The second scan is started after the set time interval from the start of the first scan. As in the first scan, projection data P1b for a plurality of views in a view angle range of θ1b corresponding to a view angle of 180° plus an X-ray fan angle α are collected as second projection data in a half scan mode, and projection data P2b for a plurality of views in a view angle range of θ2b corresponding to a view angle of 360° are collected as second projection data in a full scan mode.

After the second scan has been completed, the scan control section 30a makes a decision as to whether a next position to be scanned is present based on the input section to be imaged (S11). If a decision is made that no next position to be scanned is present, scan processing is terminated. On the other hand, a next position to be scanned next is decided to be present, the scan control section 30a outputs a control signal to the X-ray controller 25 and imaging table 4 to switch the tube voltage V for the X-ray tube 20 to the first tube voltage V1, and move the position L of the imaging table 4 to a next position L2 (S12). During the movement of the position of the imaging table 4, the rotating section 27 rotates by a rotation angle equal to (the time required to move the imaging table×360°/the cycle of rotation). That is, representing the time required to move the imaging table 4 as Tt1, it rotates by an angular range θt1 representing a rotation angle equal to (Tt1×360/Tr1) in a half scan mode, and by an angular range θt2 representing a rotation angle equal to (Tt1×360/Tr2) in a full scan mode.

After the movement of the position of the imaging table 4 has been completed, the process goes back to Step S8, and a first scan is newly started at the position L2. At that time, projection data P1c for a plurality of views in a view angle range of θ1c corresponding to a view angle of 180° plus an X-ray fan angle α are collected as first projection data at the position L2 in a half scan mode, and projection data P2c for a plurality of views in a view angle range of θ2c corresponding to a view angle of 360° are collected as first projection data at the position L2 in a full scan mode. After the switching of the tube voltage V, a second scan is performed at the position L2 in a half scan mode, and projection data P1d for a plurality of views in a view angle range of θ1d corresponding to a view angle of 180° plus an X-ray fan angle α are collected as second projection data at the position L2, and projection data P2d for a plurality of views in a view angle range of θ2d corresponding to a view angle of 360° are collected as second projection data at the position L2 in a full scan mode. After the second scan at the position L2 has been completed, a decision is made as to whether a next position to be scanned L3 is present, and if a next position L3 is present, the tube voltage V is switched, and at the same time, the position L of the imaging table 4 is moved. Upon the completion of the movement, a first scan is started at the position L3. On the other hand, if there is no next position to be scanned L3, scan processing is terminated.

After scan processing has been completed, the image producing section 30e in the central processing apparatus 30 applies reconstruction processing to the first and second projection data to produce two kinds of tomographic images representing the same slice but with different kinds of X-rays used in the scan, between which images, weighted subtraction processing is performed to produce an enhanced image such as an image in which soft tissue is principally enhanced or that in which bone tissue is principally enhanced (S13). The thus-produced enhanced image is stored in the storage device 33.

The display device 32 then displays the enhanced image of the subject 6, and several other kinds of information stored in the storage device 33 based on instructions from the central processing apparatus 30 (S14).

According to the present embodiment, a cardiac cycle of the subject 6 is identified by the cardiac cycle identifying section 30b prior to a first scan; a time interval from the start of a first scan to the start of a second scan is set by the scan start time interval setting section 30c to a time approximately the same as the aforementioned identified cardiac cycle; and the rotating section 27 is controlled by the scan control section 30a to start the first and second scans at the set time interval and perform each of the scans within one cardiac cycle while rotating the rotating section 27 in a constant cycle of rotation such that cardiac phase coverage for the first scan approximately matches that for the second scan. Therefore, two kinds of projection data can be collected by only two consecutive scans, in which data temporal changes involved in cardiac motion of the subject 6 during the scans are approximately the same as each other, that is, in which data the aforementioned temporal change of the subject 6 appears as distortion approximately the same as each other on reconstructed tomographic images, but does not appear as a difference between tomographic images. Thus, in an X-ray CT apparatus for scanning a subject 6 with two kinds of X-rays having different energy distributions, it is possible to reduce a positional offset of the subject 6 between two kinds of tomographic images representing the same slice obtained by the scans by a simple control scheme while reducing stress on the subject 6.

Moreover, according to the present embodiment, unlike a case in which an electrocardiological synchronized imaging is applied, it is not necessary to identify a cardiac phase itself and confirm it for each scan, and only a cardiac cycle may be sufficiently identified and the time interval between the start of scans can be set only once in the beginning, thus facilitating control of the scan.

Furthermore, according to the present embodiment, since the cycle-of-rotation setting section 30*d* sets a cycle of rotation of the rotating section 27 to a cycle approximately the same as the identified cardiac cycle for a half scan, or a cycle determined by subtracting the time required to switch the tube voltage from the identified cardiac cycle for a full scan, view angle ranges (positions) for first and second projection data acquired by first and second scans at the same position L can be brought as close to each other as possible, thus enabling further reduction of a positional offset of the subject 6 between two kinds of tomographic images representing the same slice.

Moreover, according to the present embodiment, projection data can be collected even in cardiac phase coverage containing a cardiac phase in which a change of the subject 6 is not slow, that is, that containing a cardiac phase other than diastolic phase. In other words, it is not necessary to collect projection data particularly aiming at a cardiac phase zone in which a change of the subject 6 is slow. This is because the present embodiment is made in an aspect that a tomographic image is obtained in which a difference based on the positional offset of the subject 6 is reduced between two kinds of tomographic images to be compared, rather than in an aspect that a tomographic image of the subject 6 is obtained in a specific cardiac phase zone or in an aspect that a tomographic image of the subject 6 is obtained free from image distortion due to subject's movement. However, when reconstruction is applied to projection data through a convolution backprojection technique or the like, and the proportion of projection data collected in a period of change of the subject 6 of the whole projection data is relatively small, variance in an image associated with the change is smoothed and image distortion based on a positional offset of the subject 6 tends to become less conspicuous in a tomographic image. Hence, the present embodiment may be considered as being made while taking advantage of such a property of the image reconstruction processing.

An X-ray CT apparatus in accordance with another embodiment of the present invention will be described.

Basically, the X-ray CT apparatus 1 in accordance with the present embodiment has generally the same configuration as the first embodiment, except the following: in the first embodiment, the scan control section 30*a* does not especially control the position of the rotating section 27 at the start of a first scan at a plurality of positions L1, L2, ..., and once the position L has been moved, a first scan is started at the moved position as soon as the movement is completed; in the present embodiment, the scan control section 30*a* is configured to match the angular position of the rotating section 27 at the start of the first scan at the plurality of positions L1, L2, ... to the same angular position. Specifically, even when the movement of the position L of the imaging table 4 has been completed, the scan control section 30*a* in the present embodiment suspends the start of the first scan until the angular position of the rotating section 27 comes again to the given position at which a previous first scan was started. Since the overall configuration of the X-ray CT apparatus 1 in accordance with the present embodiment is basically the same as that in the first embodiment shown in FIG. 1, the explanation thereof will be omitted.

Figure 8:
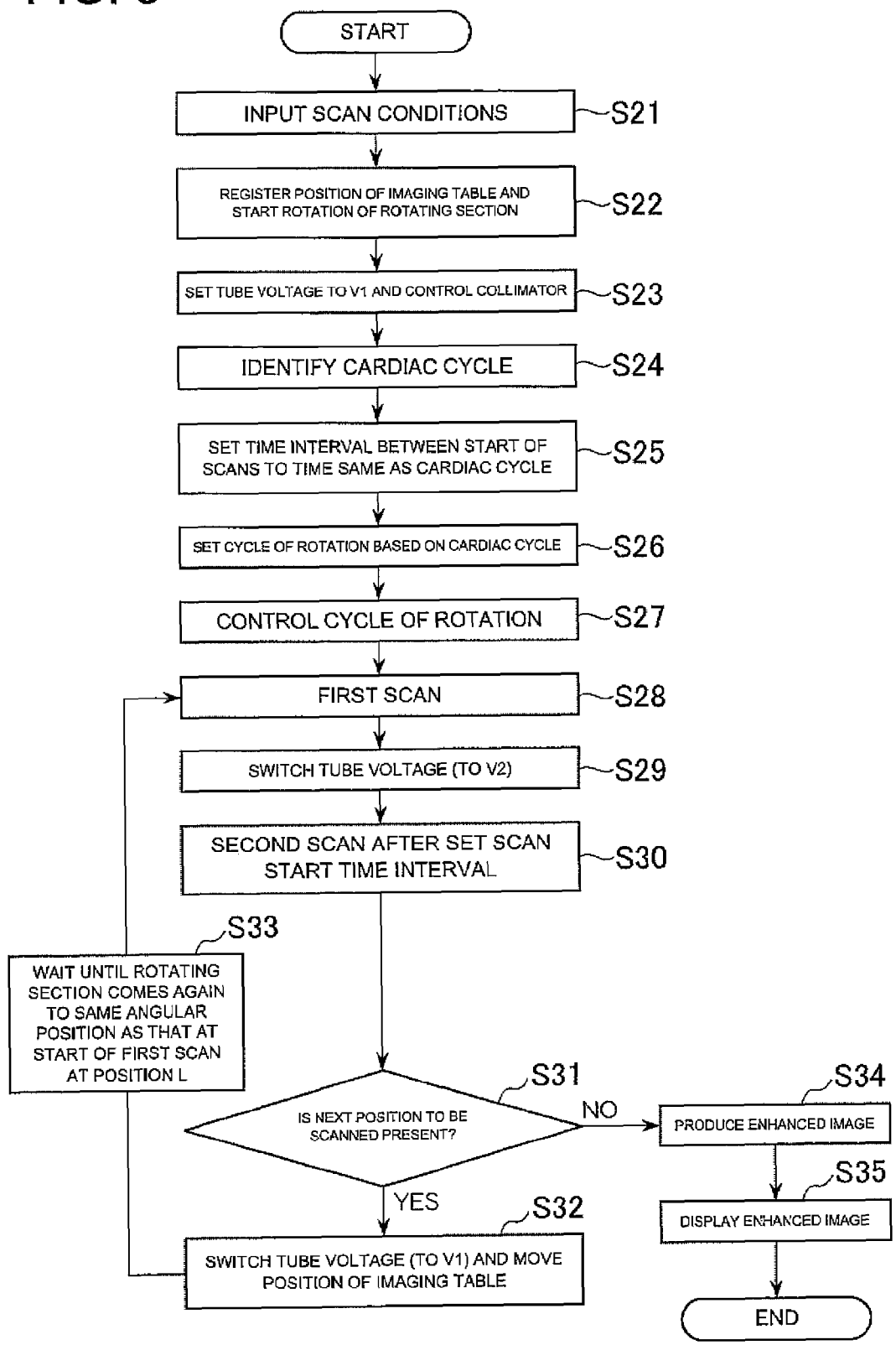
FIG. 8 is a flow chart showing an X-ray CT imaging method using an X-ray CT apparatus in accordance with another embodiment of the present invention.
Figure 9:
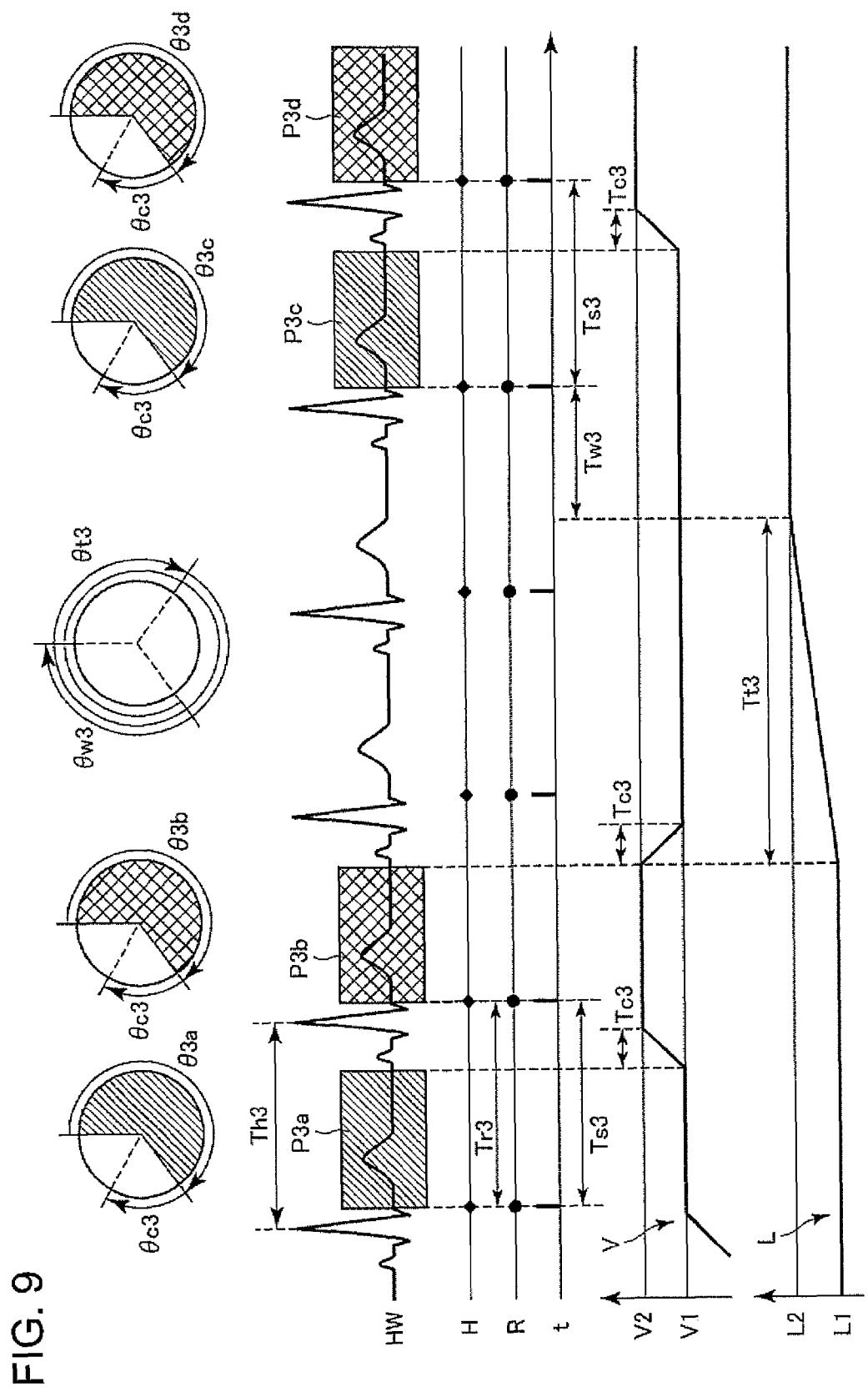
FIG. 9 is a drawing showing a time chart of scan processing in a half scan mode in accordance with another embodiment of the invention.
Figure 10:
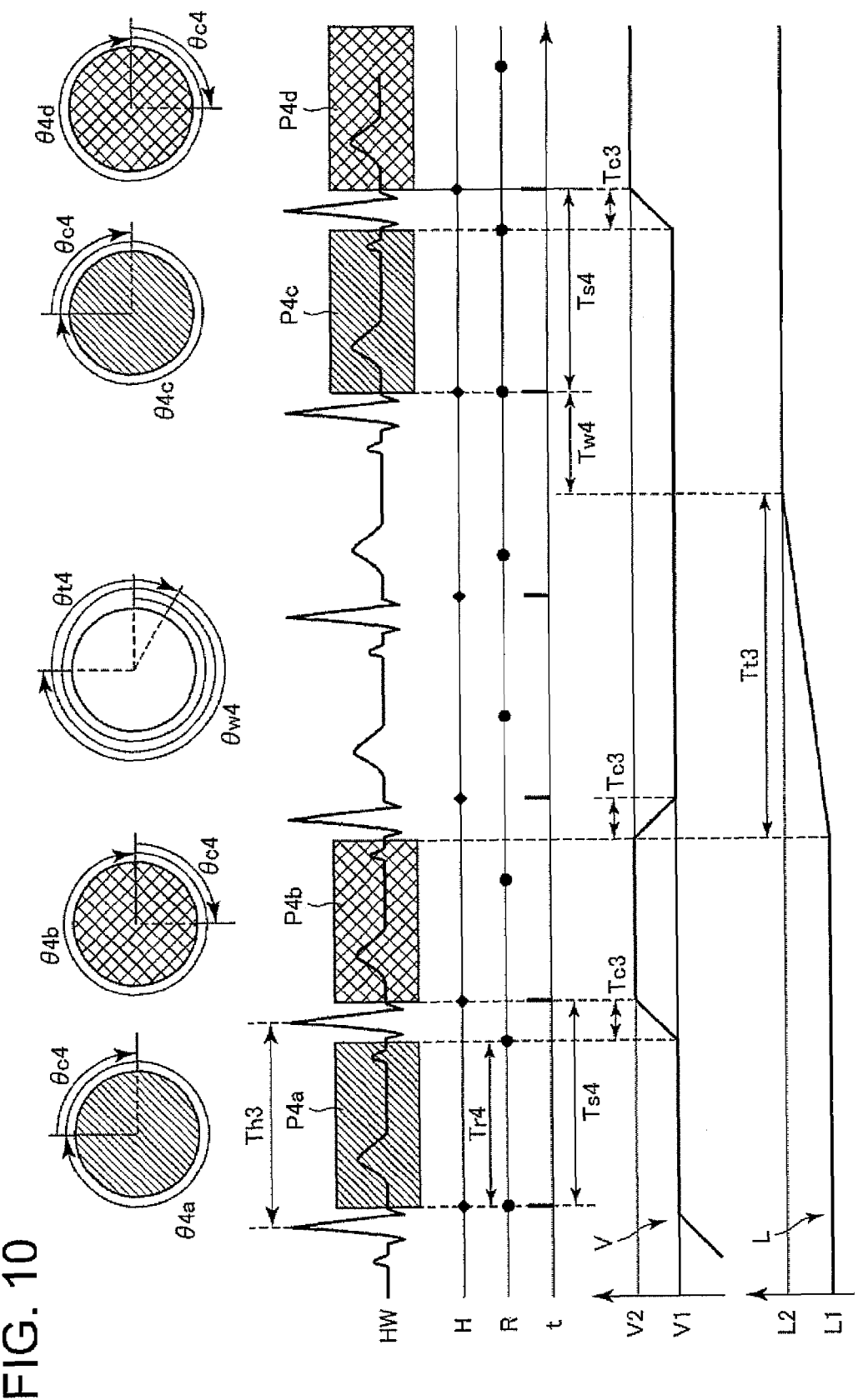
FIG. 10 is a drawing showing a time chart of scan processing in a full scan mode in accordance with another embodiment of the invention.

FIG. 8 is a flow chart showing an X-ray CT imaging method using the X-ray CT apparatus of the present embodiment. FIGS. 9 and 10 are drawings showing time charts of scan processing in accordance with the present embodiment, in which FIG. 9 represents a scan mode being a half scan mode, and FIG. 10 represents a scan mode being a full scan mode.

First, a human operator inputs several setting particulars of actual scan conditions into the input device 31, which are output to the central processing apparatus 30 (S21).

The scan control section 30*a* then outputs a control signal to the scan gantry 2 and imaging table 4 to register the position of the imaging table 4 to a position L1 for an initial scan, and at the same time, start rotation of the rotating section 27 of the scan gantry 2 (S22).

The scan control section 30*a* outputs a control signal to the X-ray controller 25 and collimator controller 26 to set the tube voltage V for the X-ray tube 20 to a first tube voltage V1, and at the same time, control the collimator 22 to appropriately shape X-rays from the X-ray tube 20 (S23).

The cardiac cycle identifying section 30*b* identifies a cardiac cycle Th of the subject 6 based on information representing a cardiac cycle acquired from the electrocardiograph 5 (S24).

The scan start time interval setting section 30*c* sets the time interval Ts from the start of a first scan to the start of a second scan to a time Ts3 that is the same as the identified cardiac cycle Th3 (S25). Moreover, the cycle-of-rotation setting section 30*d* sets the cycle of rotation Tr of the rotating section 27 to a given cycle Tr3 that is the same as the identified cardiac cycle Th3 in a half scan mode, or sets the cycle of rotation Tr of the rotating section 27 to a given cycle Tr4 determined by subtracting the time Tc3 required to switch X-rays from the identified cardiac cycle Th3 in a full scan mode (S26).

For example, when the cardiac cycle Th3=1.0 sec. (heart rate=60/minute) and the time required to switch X-rays Tc3=0.2 sec., setting is made such that the time interval between the start of scans Ts3=1.0 sec. and the cycle of rotation Tr3=1.0 sec. in a half scan mode, and the time interval between the start of scans Ts4=1.0 sec. and the cycle of rotation Tr4=1.0−0.2=0.8 sec. in a full scan mode.

The scan control section 30*a* outputs a control signal to the rotation controller 28 to control rotation such that the cycle of rotation of the rotating section 27 becomes a cycle set by the cycle-of-rotation setting section 30*d* (S27).

Once preparation has been all made, the scan control section 30*a* outputs a control signal to the X-ray controller 25 and data collecting section 24 to perform a first scan (S28). At that time, projection data P3*a* for a plurality of views in a view angle range of θ3*a* corresponding to a view angle of 180° plus an X-ray fan angle α are collected as first projection data in a half scan mode, and projection data P4*a* for a plurality of views in a view angle range of θ4*a* corresponding to a view angle of 360° are collected as first projection data in a full scan mode.

After the first scan has been completed, the scan control section 30*a* outputs a control signal to the X-ray controller 25 to switch the tube voltage V for the X-ray tube 20 to a second tube voltage V2 (S29). During the switching of the tube voltage, the rotating section 27 rotates by an angular range θc3 representing a rotation angle equal to (Tc3×360/Tr3) in a half scan mode, and by an angular range θc4 representing a rotation angle equal to (Tc3×360/Tr4) in a full scan mode.

The scan control section 30a then outputs a control signal to the X-ray controller 25 and data collecting section 24 to perform a second scan (S30). The second scan is started after the set time interval from the start of the first scan. As in the first scan, projection data P3b for a plurality of views in a view angle range of θ3b corresponding to a view angle of 180° plus an X-ray fan angle α are collected as second projection data in a half scan mode, and projection data P4b for a plurality of views in a view angle range of θ4b corresponding to a view angle of 360° are collected as second projection data in a full scan mode.

After the second scan has been completed, the scan control section 30a makes a decision as to whether a next position to be scanned is present based on the input section to be imaged (S31). If a decision is made that no next position to be scanned is present, scan processing is terminated. On the other hand, a next position to be scanned next is decided to be present, the scan control section 30a outputs a control signal to the X-ray controller 25 and imaging table 4 to switch the tube voltage V for the X-ray tube 20 to the first tube voltage V1, and move the position L of the imaging table 4 to a next position L2 (S32). During the movement of the position of the imaging table 4, and representing the time required to move the imaging table 4 as Tt3, the rotating section 27 rotates by an angular range θt3 representing a rotation angle equal to (Tt3×360/Tr3) in a half scan mode, and by an angular range θt4 representing a rotation angle equal to (Tt3×360/Tr4) in a full scan mode.

After the movement of the position of the imaging table 4 has been completed, the process goes back to Step S28. At that time, the scan control section 30a is kept waiting until the angular position of the rotating section 27 comes back to the given angular position the same as that at which the first scan was started at the position L1 (S33), and once the angular position of the rotating section 27 comes back to that position, a first scan at a position L2 is started. In FIGS. 9 and 10, Tw3 and Tw4 represent the wait time, and θc3 and θc4 represent the angle of rotation of the rotating section 27 during the wait time. In the first scan, projection data P3c for a plurality of views in a view angle range of θ3c corresponding to a view angle of 180° plus an X-ray fan angle α are collected as first projection data at the position L2 in a half scan mode, and projection data P4c for a plurality of views in a view angle range of θ4c corresponding to a view angle of 360° are collected as first projection data at the position L2 in a full scan mode. After the switching of the tube voltage V, a second scan is performed at the position L2, and projection data P3d for a plurality of views in a view angle range of θ3d corresponding to a view angle of 180° plus an X-ray fan angle α are collected as second projection data at the position L2 in a half scan mode, and projection data P4d for a plurality of views in a view angle range of θ4d corresponding to a view angle of 360° are collected as second projection data at the position L2 in a full scan mode. After the second scan at the position L2 has been completed, a decision is made as to whether a next position to be scanned L3 is present, and if a next position L3 is present, the tube voltage V is switched, and at the same time, the position L of the imaging table 4 is moved. After the movement is completed, a first scan is started at the position L3 when the angular position of the rotating section 27 comes back to the aforementioned given position. On the other hand, if there is no next position to be scanned L3, scan processing is terminated.

Since the processing (S34-S35) after the termination of the scan processing is the same as that in the first embodiment, the explanation thereof will be omitted.

According to the present embodiment as described above, since the scan control section 30a matches the angular position of the rotating section 27 at the start of a first scan at a plurality of positions L1, L2, . . . to the same angular position, projection data corresponding to the cardiac phases and view angle ranges approximately the same as each other at a plurality of positions L1, L2, . . . , that is, projection data having a change pattern of the subject 6 associated with cardiac motion appearing as image features generally similar to each other on reconstructed tomographic images, can be collected. Thus, in comparing tomographic images obtained by scans at different positions L, for example, comparison can be made between tomographic images having less image fluctuations due to a change of the subject 6 associated with cardiac motion; and in generating volume data based on such tomographic images, volume data in which distortion in an image due to such a change is suppressed can be generated. Especially, it is difficult to smooth a change of the subject 6 in reconstruction for a half scan because there is no projection data in a conjugate view, unlike for a full scan, and a tomographic image is susceptible to such a change; thus, the present embodiment has a greater effect in such a case.

An X-ray CT apparatus in accordance with still another embodiment of the present invention will be described.

Basically, the X-ray CT apparatus 1 in accordance with the present embodiment has generally the same configuration as the first embodiment, except the following: in the first embodiment, the cycle-of-rotation setting section 30d sets the cycle of rotation Tr of the rotating section 27 to a given cycle based on an identified cardiac cycle Th1; in this embodiment, the cycle-of-rotation setting section 30a is configured to set the cycle of rotation Tr of the rotating section 27 to an appropriate cycle independently of the identified cardiac cycle Th1. Since the overall configuration of the X-ray CT apparatus 1 in accordance with the present embodiment is basically the same as that in the first embodiment shown in FIG. 1, the explanation thereof will be omitted.

Now an X-ray CT imaging method using the X-ray CT apparatus 1 in accordance with the present embodiment will be described.

Figure 11:
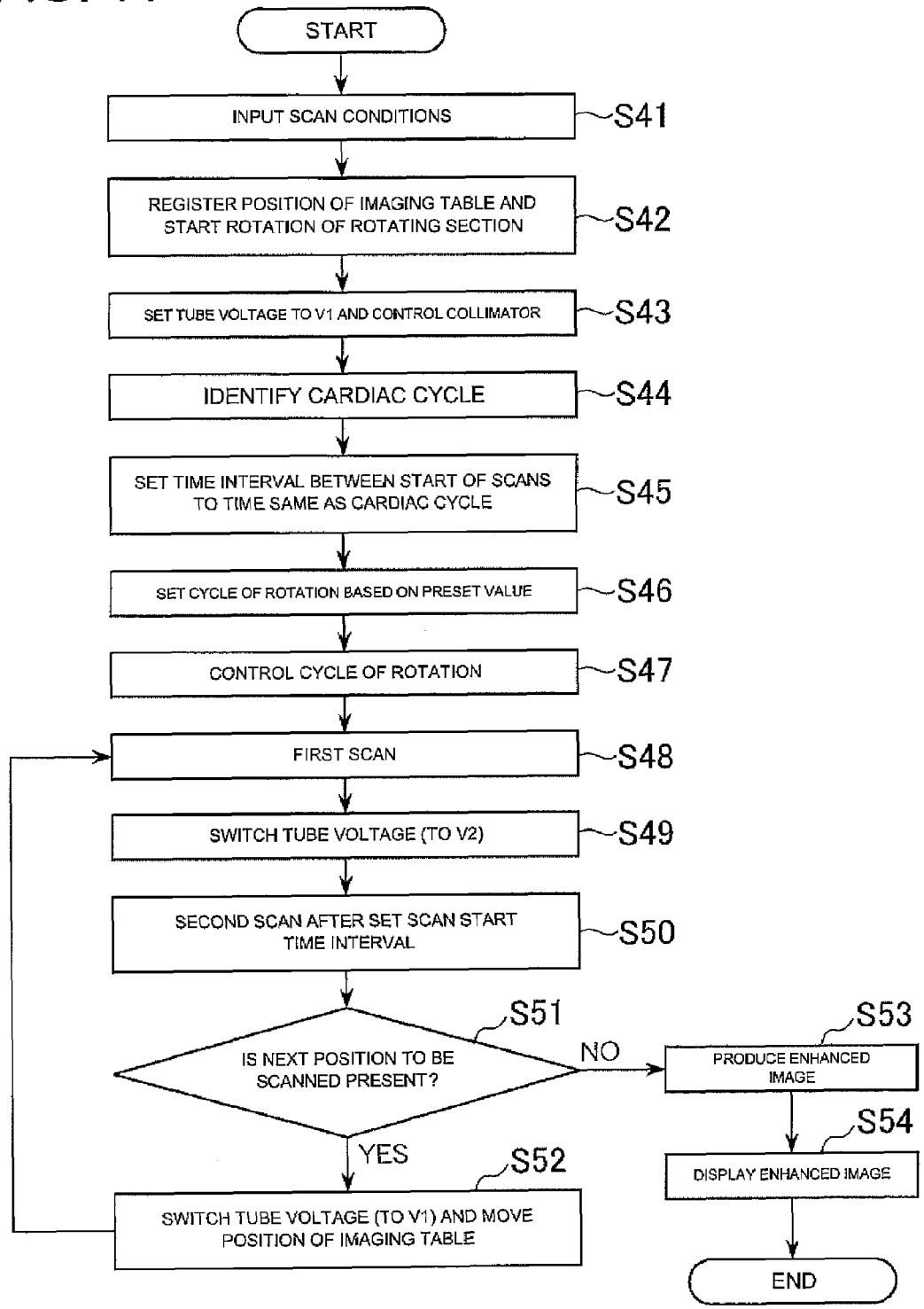
FIG. 11 is a flow chart showing an X-ray CT imaging method using an X-ray CT apparatus in accordance with still another embodiment of the present invention.
Figure 12:
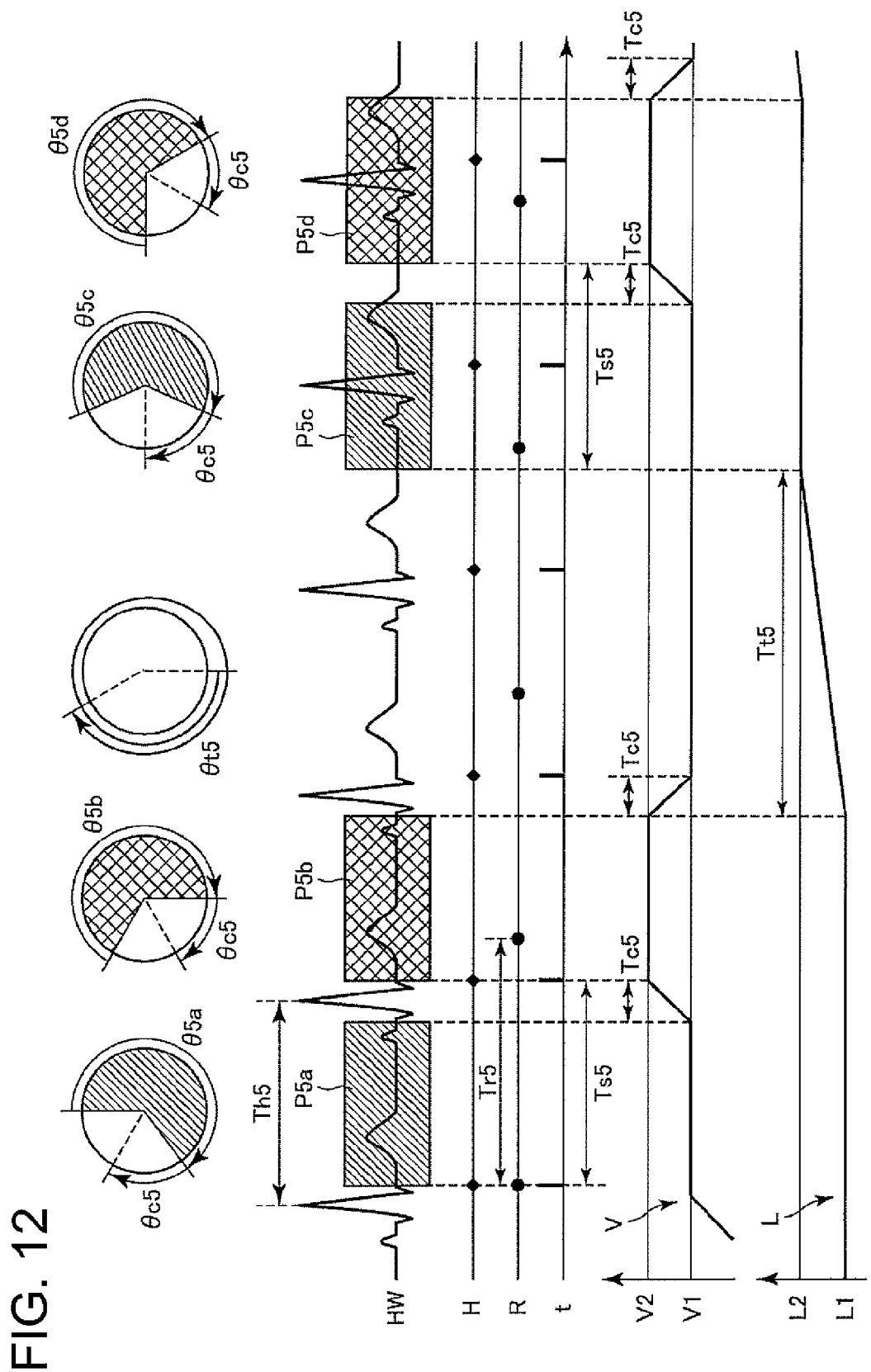
FIG. 12 is a drawing showing a time chart of scan processing in a half scan mode in accordance with still another embodiment of the present invention.
Figure 13:
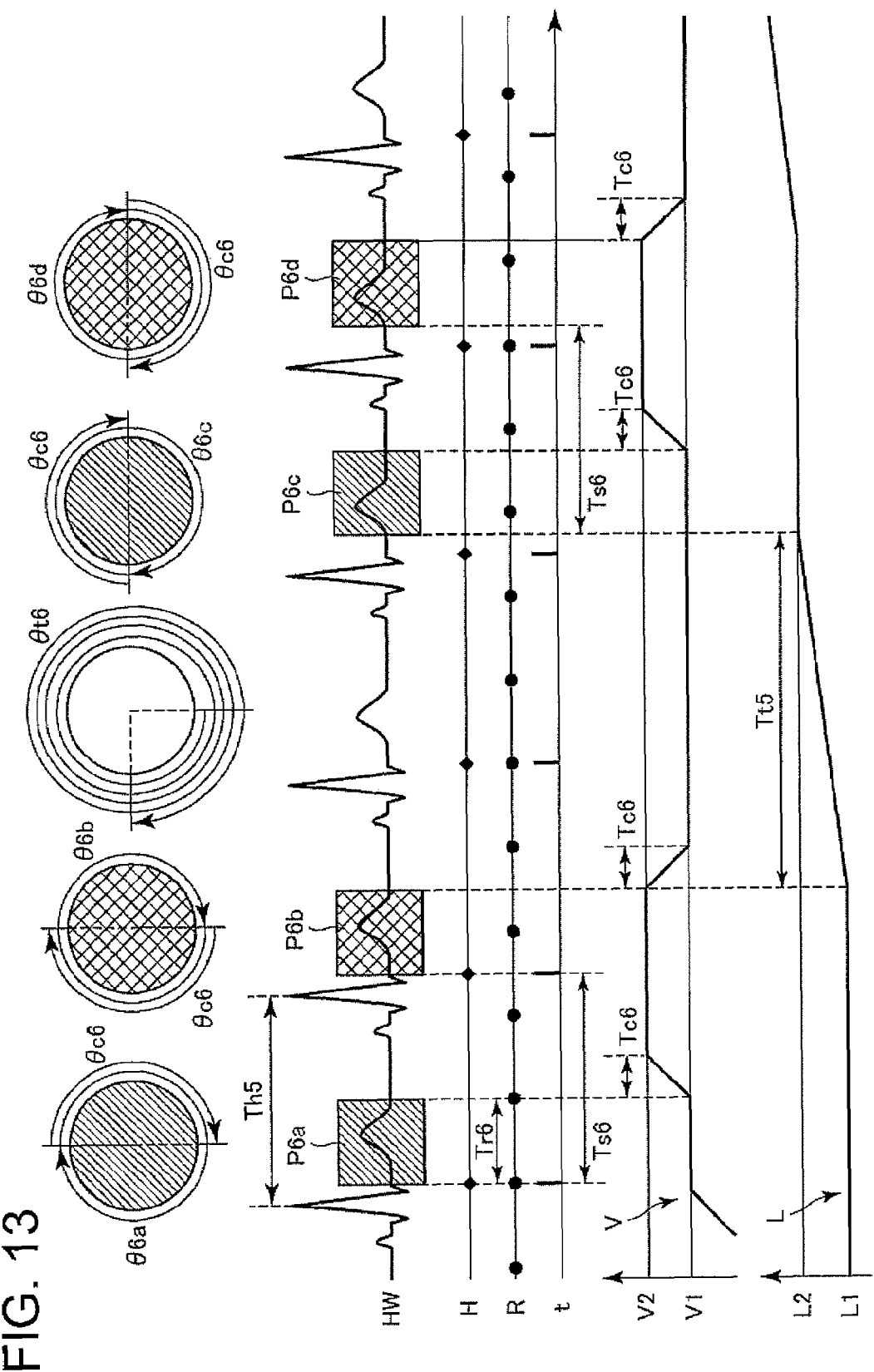
FIG. 13 is a drawing showing a time chart of scan processing in a full scan mode in accordance with still another embodiment of the present invention.

FIG. 11 is a flow chart showing an X-ray CT imaging method using the X-ray CT apparatus of the present embodiment. FIGS. 12 and 13 are drawings showing time charts of scan processing in accordance with the present embodiment, in which FIG. 12 represents a scan mode being a half scan mode, and FIG. 13 represents a scan mode being a full scan mode.

First, a human operator inputs several setting particulars of actual scan conditions into the input device 31, which are output to the central processing apparatus 30 (S41).

The scan control section 30a in the central processing section 30 then outputs a control signal to the scan gantry 2 and imaging table 4 to register the position of the imaging table 4 to a position L1 for an initial scan, and at the same time, start rotation of the rotating section 27 of the scan gantry 2 (S42).

The scan control section 30a outputs a control signal to the X-ray controller 25 and collimator controller 26 to set the tube voltage V for the X-ray tube 20 to a first tube voltage V1, and at the same time, control the collimator 22 to appropriately shape X-rays from the X-ray tube 20 (S43).

The cardiac cycle identifying section 30b identifies a cardiac cycle Th of the subject 6 based on information representing a cardiac cycle acquired from the electrocardiograph 5 (S44).

The scan start time interval setting section 30c sets the time interval Ts between the start of scans to a cycle Ts5 that is the same as the identified cardiac cycle Th5 (S45). Moreover, the cycle-of-rotation setting section 30d sets the cycle of rotation Tr of the rotating section 27 to an appropriate cycle. For example, it sets the cycle of rotation Tr to a preset cycle Tr5 in a half scan mode, and to a preset cycle Tr6 in a full scan mode (S46).

For example, when the cardiac cycle Th5=1.0 sec. (heart rate=60/minute) and the time required to switch X-rays Tc5=0.2 sec., setting is made such that the time interval between the start of scans Ts5=1.0 sec. and the cycle of rotation Tr5=1.2 sec. in a half scan mode, and the time interval between the start of scans Ts6=1.0 sec. and the cycle of rotation Tr6=0.4 sec. in a full scan mode.

The scan control section 30a outputs a control signal to the rotation controller 28 to control rotation such that the cycle of rotation of the rotating section 27 becomes a cycle set by the cycle-of-rotation setting section 30d (S47).

Once preparation has been all made, the scan control section 30a outputs a control signal to the X-ray controller 25 and data collecting section 24 to perform a first scan (S48). At that time, projection data P5a for a plurality of views in a view angle range of θ5a corresponding to a view angle of 180° plus an X-ray fan angle α are collected as first projection data in a half scan mode, and projection data P6a for a plurality of views in a view angle range of θ6a corresponding to a view angle of 360° are collected as first projection data in a full scan mode.

After the first scan has been completed, the scan control section 30a outputs a control signal to the X-ray controller 25 to switch the tube voltage V for the X-ray tube 20 to a second tube voltage V2 (S49). During the switching of the tube voltage, the rotating section 27 rotates by a rotation angle equal to (the time required to switch the tube voltage×360°/the cycle of rotation). Specifically, it rotates by an angular range θc5 representing a rotation angle equal to (Tc5×360/Tr5) in a half scan mode, and by an angular range θc6 representing a rotation angle equal to (Tc6×360/Tr6) in a full scan mode.

The scan control section 30a then outputs a control signal to the X-ray controller 25 and data collecting section 24 to perform a second scan (S50). The second scan is started after the set time interval from the start of the first scan. As in the first scan, projection data P5b for a plurality of views in a view angle range of θ5b corresponding to a view angle of 180° plus an X-ray fan angle α are collected as second projection data in a half scan mode, and projection data P6b for a plurality of views in a view angle range of θ6b corresponding to a view angle of 360° are collected as second projection data in a full scan mode.

After the second scan has been completed, the scan control section 30a makes a decision as to whether a next position to be scanned is present based on the input section to be imaged (S51). If a decision is made that no next position to be scanned is present, scan processing is terminated. On the other hand, a next position to be scanned next is decided to be present, the scan control section 30a outputs a control signal to the X-ray controller 25 and imaging table 4 to switch the tube voltage V for the X-ray tube 20 to the first tube voltage V1, and move the position L of the imaging table 4 to a next position L2 (S32). During the movement of the position of the imaging table 4, the rotating section 27 rotates by a rotation angle equal to (the time required to move the imaging table×360°/the cycle of rotation). Specifically, representing the time required to move the imaging table 4 as Tt5, the rotating section 27 rotates by an angular range θt5 representing a rotation angle equal to (Tt5×360/Tr5) in a half scan mode, and by an angular range θt6 representing a rotation angle equal to (Tt5×360/Tr6) in a full scan mode.

After the movement of the position of the imaging table 4 has been completed, the process goes back to Step S48, and a first scan is newly started at the position L2. At that time, projection data P5c for a plurality of views in a view angle range of θ5c corresponding to a view angle of 180° plus an X-ray fan angle α are collected as first projection data at the position L2 in a half scan mode, and projection data P6c for a plurality of views in a view angle range of θ6c corresponding to a view angle of 360° are collected as first projection data at the position L2 in a full scan mode. After the switching of the tube voltage V, a second scan is performed at the position L2, and projection data P5d for a plurality of views in a view angle range of θ5d corresponding to a view angle of 180° plus an X-ray fan angle α are collected as second projection data at the position L2 in a half scan mode, and projection data P6d for a plurality of views in a view angle range of θ6d corresponding to a view angle of 360° are collected as second projection data at the position L2 in a full scan mode. After the second scan at the position L2 has been completed, a decision is made as to whether a next position to be scanned L3 is present, and if a next position L3 is present, the tube voltage V is switched, and at the same time, the position L of the imaging table 4 is moved. Upon the completion of the movement, a first scan is started at the position L3. On the other hand, if there is no next position to be scanned L3, scan processing is terminated.

Since the processing (S53-S54) after the termination of the scan processing is the same as that in the first embodiment, the explanation thereof will be omitted.

According to the present embodiment as described above, since the cycle of rotation Tr of the rotating section 27 is set to an appropriate cycle independently of the identified cardiac cycle Th1, the cycle of rotation Tr can be freely set or fixed according to circumstances. For example, when performing first and second scans at a set time interval between the start of scans, the cycle of rotation Tr may be set to start the second scan immediately after the switching of the tube voltage V after the first scan, so that the time for one scan can be reserved as long as possible, enabling further improvement of image quality of the resulting tomographic image.

An X-ray CT apparatus in accordance with yet still another embodiment of the present invention will be described.

Basically, the X-ray CT apparatus 1 in accordance with the present embodiment has generally the same configuration as the first embodiment, except the following: in the first embodiment, the scan start time interval setting section 30c and cycle-of-rotation setting section 30d set the time interval Ts between the start of scans and the cycle of rotation Tr of the rotating section 27 based on an identified cardiac cycle Th prior to the start of an initial scan, and the scan control section 30a performs a scan at a plurality of positions L1, L2, ... at the same time interval and in the same cycle of rotation; in this embodiment, the cardiac cycle identifying section 30b is configured to identify a cardiac cycle Th of the subject 6 at least each time the position L is moved, the scan start time interval setting section 30c is configured to set the time interval Ts between the start of scans to a cycle approximately the same as the latest identified cardiac cycle Th each time the position L is moved, and the cycle-of-rotation setting section 30d is configured to set the cycle of rotation Tr to a given cycle based on the latest cardiac cycle each time the position L is moved. More particularly, in the present embodiment, the cardiac cycle identifying section 30b is configured to identify a cardiac cycle Th of the subject 6 while the position L is being moved to a next position, the cycle-of-rotation setting section 30d is configured to set a given cycle based on the latest identified cardiac cycle Th while the position L is being moved to the next position, and the scan control section 30a is configured to start control to bring the cycle of rotation Tr close to the set cycle of rotation while the position L is being moved to the next position.

Now an X-ray CT imaging method using the X-ray CT apparatus 1 in accordance with the present embodiment will be described.

Figure 14:
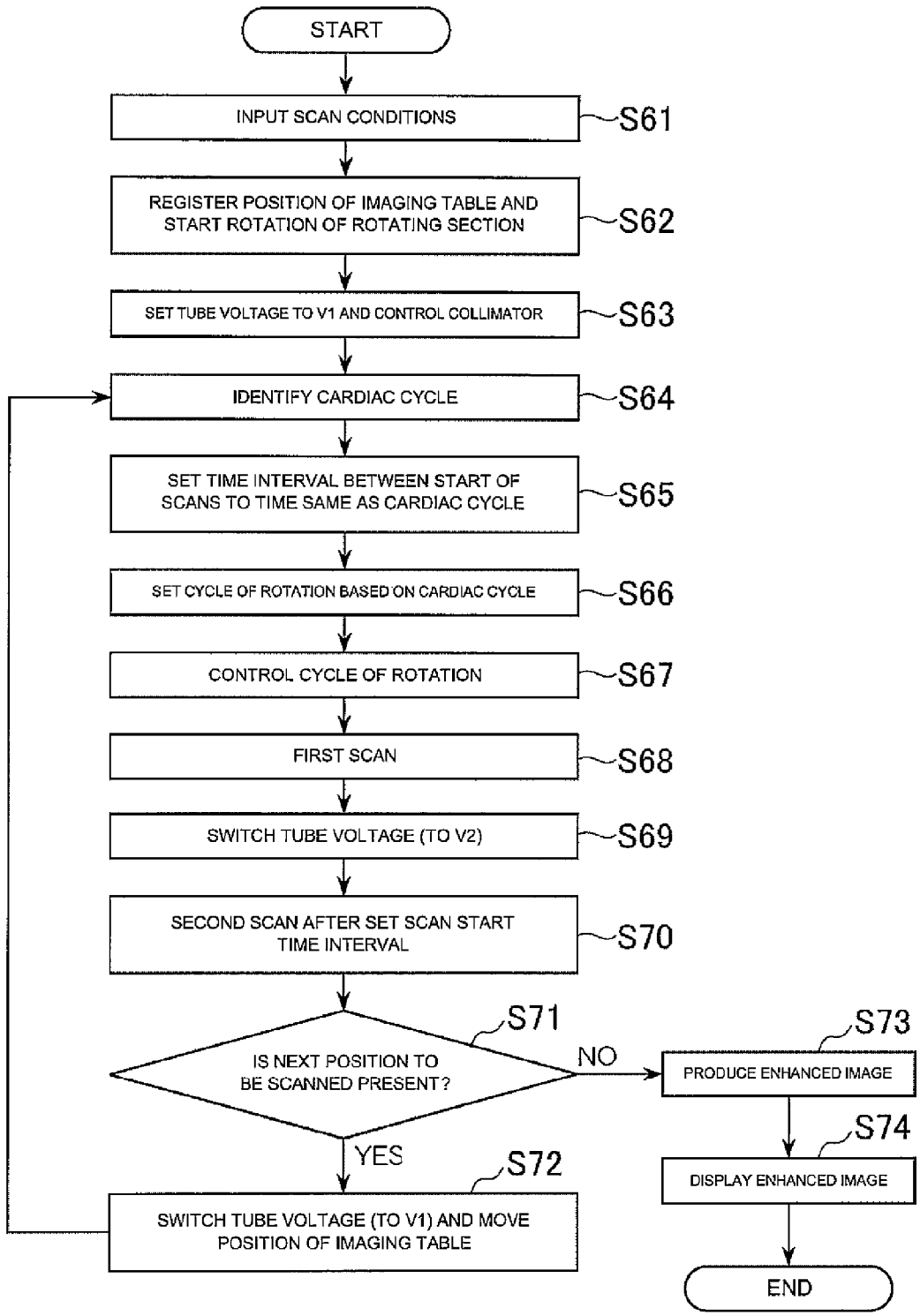
FIG. 14 is a flow chart showing an X-ray CT imaging method using an X-ray CT apparatus in accordance with yet still another embodiment of the present invention.
Figure 15:
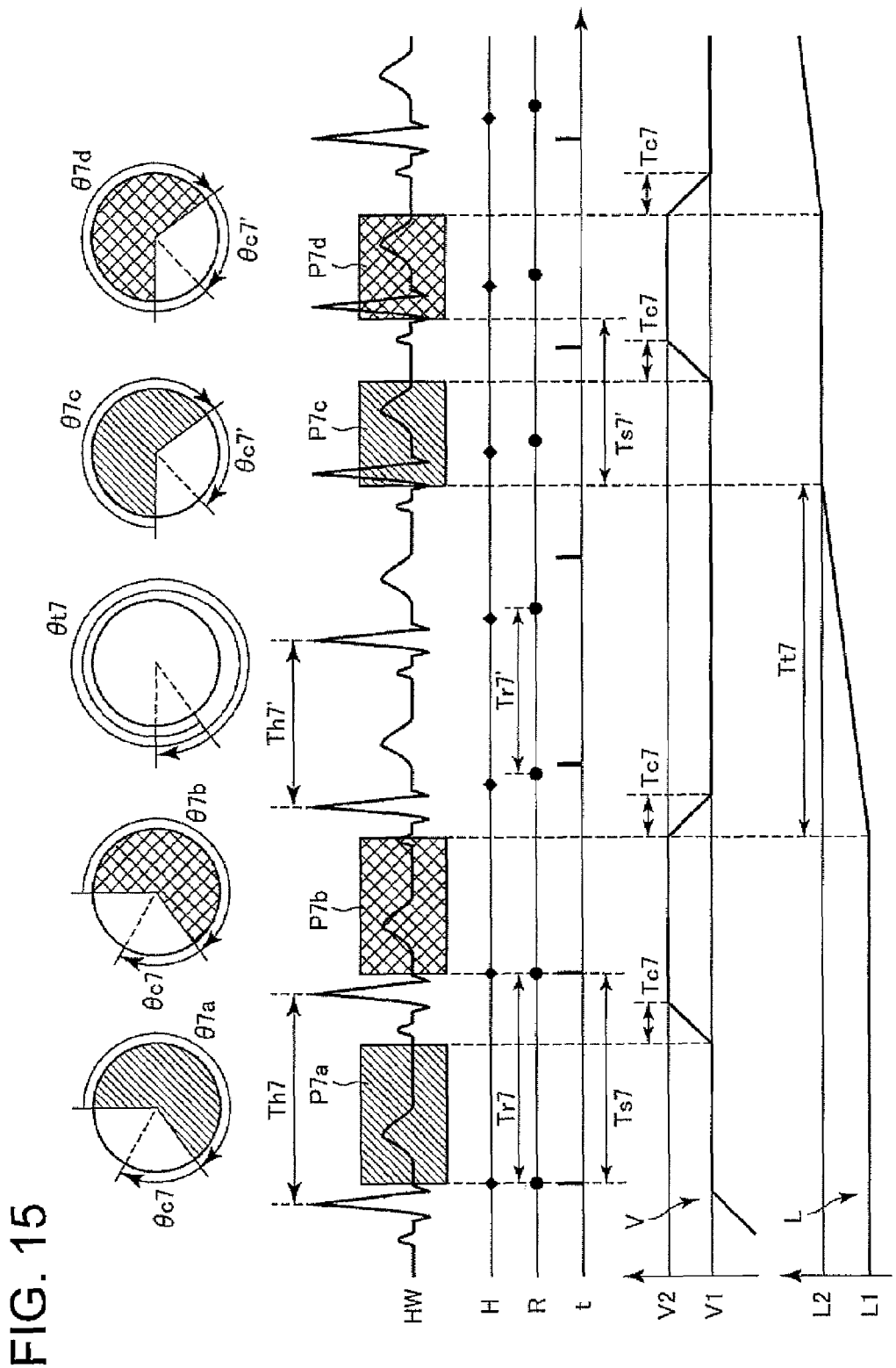
FIG. 15 is a drawing showing a time chart of scan processing in a half scan mode in accordance with yet still another embodiment of the present invention.

FIG. 14 is a flow chart showing an X-ray CT imaging method using the X-ray CT apparatus of the present embodiment. FIG. 15 is a drawing showing a time chart of scan processing in accordance with the present embodiment in a half scan mode.

First, a human operator inputs several setting particulars of actual scan conditions into the input device 31, which are output to the central processing apparatus 30 (S61).

The scan control section 30a then outputs a control signal to the scan gantry 2 and imaging table 4 to register the position of the imaging table 4 to a position L1 for an initial scan, and at the same time, start rotation of the rotating section 27 of the scan gantry 2 (S62).

The scan control section 30a outputs a control signal to the X-ray controller 25 and collimator controller 26 to set the tube voltage V for the X-ray tube 20 to a first tube voltage V1, and at the same time, control the collimator 22 to appropriately shape X-rays from the X-ray tube 20 (S63).

The cardiac cycle identifying section 30b identifies a cardiac cycle Th of the subject 6 based on information representing a cardiac cycle acquired from the electrocardiograph 5 (S64).

The scan start time interval setting section 30c sets a time interval Ts between the start of scans to a time Ts7 that is the same as the identified cardiac cycle Th7 (S65). Moreover, the cycle-of-rotation setting section 30d sets the cycle of rotation Tr of the rotating section 27 to a given cycle Tr7 that is the same as the identified cardiac cycle Th7 (S66).

For example, when the cardiac cycle Th7=1.0 sec. (heart rate=60/minute) and the time required to switch X-rays Tc7=0.2 sec., setting is made such that the time interval between the start of scans Ts7=1.0 sec. and the cycle of rotation Tr7=1.0 sec.

The scan control section 30a outputs a control signal to the rotation controller 28 to control rotation such that the cycle of rotation of the rotating section 27 becomes a cycle set by the cycle-of-rotation setting section 30d (S67).

Once preparation has been all made, the scan control section 30a outputs a control signal to the X-ray controller 25 and data collecting section 24 to perform a first scan (S68). At that time, projection data P7a for a plurality of views in a view angle range of θ7a corresponding to a view angle of 180° plus an X-ray fan angle α are collected as first projection data.

After the first scan has been completed, the scan control section 30a outputs a control signal to the X-ray controller 25 to switch the tube voltage V for the X-ray tube 20 to a second tube voltage V2 (S69). During the switching of the tube voltage, the rotating section 27 rotates by an angular range θc7 representing a rotation angle equal to (Tc7×360/Tr7).

The scan control section 30a then outputs a control signal to the X-ray controller 25 and data collecting section 24 to perform a second scan (S70). The second scan is started after the set time interval from the start of the first scan. As in the first scan, projection data P7b for a plurality of views in a view angle range of θ7b corresponding to a view angle of 180° plus an X-ray fan angle α are collected as second projection data.

After the second scan has been completed, the scan control section 30a makes a decision as to whether a next position to be scanned is present based on the input section to be imaged (S71). If a decision is made that no next position to be scanned is present, scan processing is terminated. On the other hand, a next position to be scanned next is decided to be present, the scan control section 30a outputs a control signal to the X-ray controller 25 and imaging table 4 to switch the tube voltage V for the X-ray tube 20 to the first tube voltage V1, and moves the position L of the imaging table 4 to a next position L2 (S72). During the movement of the position of the imaging table 4, and representing the time required to move the imaging table 4 as Tt7, the rotating section 27 rotates by an angular range θt7 representing a rotation angle equal to (Tt7×360/Tr7).

The process then goes back to Step S64, and the scan control section 30a outputs a control signal to the cardiac cycle identifying section 30b, scan start time interval setting section 30c, and cycle-of-rotation setting section 30d while the position L of the imaging table 4 is being moved to the next position L2. While the position L is being moved to the position L2, i.e., during movement of the imaging table 4, the cardiac cycle identifying section 30b identifies a cardiac cycle Th of the subject 6, the scan start time interval setting section 30c sets the time interval Ts between the start of scans to a time Ts7' approximately the same as the latest identified cardiac cycle Th7' (S65), and the cycle-of-rotation setting section 30d sets the cycle of rotation Tr to a cycle Tr7' approximately the same as the latest identified cardiac cycle Th7' (S66).

The scan control section 30a then starts control to bring the cycle of rotation Tr of the rotating section 27 close to the set cycle of rotation Tr7' (S67), and sets the cycle of rotation Tr of the rotating section 27 to the newly set cycle of rotation Tr7' before the movement of the position of the imaging table 4 is completed.

Immediately after the movement of the position of the imaging table 4 has been completed, the scan control section 30a outputs a control signal to the X-ray controller 25 and data collecting section 24 to start a first scan (S68).

Thereafter, these steps are repeated following the aforementioned flow until no position to be scanned is left. Since the processing (S73-S74) after the completion of the scan processing is the same as that in the first embodiment, the explanation thereof will be omitted.

According to the present embodiment as described above, since the cardiac cycle Th of the subject 6 is identified each time the position L is moved, and the time interval Ts between the start of scans and the cycle of rotation Tr of the rotating section 27 are updated, the time interval Ts and cycle of rotation Tr can be made to follow a given cycle determined based on an actual cardiac cycle. Therefore, even in the case that the cardiac cycle Th varies with time, the cardiac phase coverage for first and second projection data at the same position L can be kept in approximately the same coverage.

While a scan is performed at a plurality of positions L1, L2, . . . in the aforementioned embodiments, it will be easily recognized that a scan may be performed only at a single position.

Moreover, while two kinds of X-rays are employed in the aforementioned embodiments, X-ray CT imaging may be performed with three or more kinds of X-rays.

Furthermore, X-rays are administered to the subject in the aforementioned embodiments, other radiation, for example, gamma rays, may be employed.

The aforementioned embodiments are provided merely by way of example of the best mode for carrying out the present invention, and the present invention is not limited to these embodiments. That is, all variations, additions and combinations are possible in the present invention insofar as they are not deviated from the spirit of the present invention.

In addition, a program that causes a computer to serve as the scan control device, scan start time interval setting device and cycle-of-rotation setting device in the present invention may constitute an exemplary embodiment of the present invention. It should be noted that such a program may be supplied by downloading or distributing it via a network such as the Internet, or by recording it in a computer-readable recording medium.

The invention claimed is:

1. An X-ray Computed Tomography (CT) apparatus comprising:
   an X-ray data collecting system comprising an X-ray generating section configured to generate X-rays and an X-ray detecting section comprising a large number of X-ray detector elements one of one-dimensionally arranged and two-dimensionally arranged, wherein said X-ray generating section faces said X-ray detecting section across a cavity, and wherein said X-ray data collecting system is oriented rotatably around a given axis;
   an imaging table configured to carry a subject placed thereon through the cavity along the given axis; and
   a scan control device configured to control said X-ray data collecting system and said imaging table to sequentially perform a first scan and a second scan with switched X-rays generated by said X-ray generating section, the first scan collecting projection data at a given position in a direction of the given axis over a given view angle sufficient for reconstruction processing for a tomographic image with first X-rays having a first energy distribution, and the second scan collecting projection data over the given view angle with second X-rays having a second energy distribution different from said first energy distribution, said scan control device further configured to control a cycle of rotation of said X-ray data collecting system such that:
      a required time for rotating an angle range is at least a time required to switch the X-rays and, when added to the given view angle, is approximately equal to a cardiac cycle of the subject;
      a time interval from a start of the first scan to a start of the second scan is approximately equal to a time of the cardiac cycle of the subject; and
      each of the first and second scans is performed within one cardiac cycle, such that a first cardiac phase coverage in the first scan approximately matches a second cardiac phase coverage in the second scan.

2. The X-ray CT apparatus as defined by claim 1, wherein:
   the given view angle is an angle of 180° plus a fan angle of the X-rays; and
   said scan control device is configured to control the cycle of rotation of said X-ray data collecting system to a given cycle approximately the same as the cardiac cycle.

3. The X-ray CT apparatus as defined by claim 1, wherein:
   the given view angle is 360°; and
   said scan control device is configured to control the cycle of rotation of said X-ray data collecting system to a given cycle approximately the same as a cycle determined by subtracting a time required to switch the X-rays from the cardiac cycle.

4. The X-ray CT apparatus as defined by claim 1, wherein:
   said scan control device is configured to control said X-ray data collecting system and said imaging table to sequentially move the given position to a plurality of positions arranged in a direction of the given axis and to perform the first scan and the second scan at each of the positions.

5. The X-ray CT apparatus as defined by claim 4, wherein:
   said scan control device is configured to control said X-ray data collecting system to perform the first scan and the second scan at the plurality of positions all at the same the time interval and in the same the cycle of rotation.

6. The X-ray CT apparatus as defined by claim 4, wherein:
   said scan control device is configured to control said X-ray data collecting system to match the angular position of said X-ray data collecting system at the start of the first scan all to the same angular position at the plurality of positions.

7. The X-ray CT apparatus as defined by claim 1, wherein:
   said scan control device is configured to control said X-ray data collecting system and said imaging table to sequentially move the given position to a plurality of positions arranged in a direction of the given axis, and to perform the first scan and the second scan at each of the positions.

8. The X-ray CT apparatus as defined by claim 7, wherein:
   said scan control device is configured to control said X-ray data collecting system to start the first scan and the second scan all at the same time interval at the plurality of positions.

9. The X-ray CT apparatus as defined by claim 7, wherein:
   said cardiac cycle identifying device is configured to identify a cardiac cycle of the subject each time the given position is moved; and
   said scan start time interval setting device is configured to set the time interval to a time approximately the same as the identified cardiac cycle each time the given position is moved.

10. The X-ray CT apparatus as defined by claim 1, further comprising:
    an image producing device configured to process first projection data acquired by the first scan and second projection data acquired by the second scan to produce an enhanced image in which a difference between a tomographic image from the first projection data and a tomographic image from the second projection data representing mutually the same slice is enhanced.

11. The X-ray CT apparatus as defined by claim 10, wherein:
    said image producing device is configured to apply reconstruction processing to the first projection data to obtain a first tomographic image, to apply reconstruction processing to the second projection data to obtain a second tomographic image, and to perform inter-image computational processing between the first tomographic image and the second tomographic image to produce the enhanced image.

12. The X-ray CT apparatus as defined by claim 11, wherein:
    the inter-image computational processing is one of addition processing and subtraction processing.

13. The X-ray CT apparatus as defined by claim 1, further comprising:
    a cardiac cycle identifying device configured to identify the cardiac cycle of the subject prior to the first scan;
    a scan start time interval setting device configured to set the time interval from the start of the first scan to the start of the second scan to a time approximately the same as the identified cardiac cycle; and
    a cycle-of-rotation setting device configured to set the cycle of rotation such that the required time for rotating the angle range of at least the time required to switch the X-rays added to the given view angle is approximately equal to the cardiac cycle of the subject, wherein said scan control device is further configured to control said X-ray data collecting system and said imaging table based on the time interval and the cycle of rotation.

14. The X-ray CT apparatus as defined by claim 13, wherein:
said scan control device is configured to cause said X-ray data collecting system and said imaging table to move the given position to a plurality of positions arranged in the direction of the given axis, and to perform the first and second scans at each of the plurality of positions;
said cardiac cycle identifying device is configured to identify the cardiac cycle of the subject each time the given position is moved;
said scan start time interval setting device is configured to set the time interval to a time approximately the same as the identified cardiac cycle each time the given position is moved; and
said cycle-of-rotation setting device is configured to set the cycle of rotation to the given cycle based on the cardiac cycle each time the given position is moved.

15. The X-ray CT apparatus as defined by claim 14, wherein:
said cardiac cycle identifying device is configured to identify a cardiac cycle of the subject while the given position is being moved to a next position;
said cycle-of-rotation setting device is configured to set the given cycle based on the identified cardiac cycle while the given position is being moved to a next position; and
said scan control device is configured to control said X-ray data collecting system such that said X-ray data collecting system brings the cycle of rotation close to the set given cycle while the given position is being moved to a next position.

16. The X-ray CT apparatus as defined by claim 1, wherein:
said scan control device is configured to control said X-ray data collecting system and said imaging table without synchronizing with either of the first cardiac phase coverage or the second cardiac phase coverage based on an electrocardiograph of the subject.

17. A method for scanning a subject using an X-ray Computed Tomography (CT) apparatus, said method comprising:
rotating an X-ray data collecting system about the subject, the X-ray data collecting system including an X-ray generating section configured to generate X-rays and an X-ray detecting system positioned across a cavity from the X-ray generating section, the X-ray detecting system including a plurality of X-ray detector elements arranged in one of a one-dimensional arrangement and a two-dimensional arrangement;
identifying a cardiac cycle of the subject prior to a first scan;
setting a cycle of rotation of the X-ray data collecting system such that a required time for rotating an angle range is at least a time required to switch the X-rays and, when added to the given view angle, is approximately equal to a cardiac cycle of the subject; and
controlling the X-ray data collecting system and the imaging table such that:
a time interval from a start of the first scan to a start of the second scan is approximately equal to a time of the cardiac cycle of the subject; and
a first cardiac phase coverage in the first scan approximately matches a second cardiac phase coverage in the second scan, the first scan including projection data collected at a given position in a direction of a given axis over a given view angle sufficient for reconstruction processing for a tomographic image with first X-rays having a first energy distribution, and the second scan including projection data collected over the given view angle with second X-rays having a second energy distribution different from said first energy distribution.

18. The method as defined by claim 17, wherein:
the given view angle is an angle of 180° plus a fan angle of the X-rays; and
setting a cycle of rotation comprises setting the cycle of rotation approximately equal to the identified cardiac cycle.

19. The method as defined by claim 17, wherein:
the given view angle is an angle of 360°; and
setting a cycle of rotation comprises determining the cycle of rotation by subtracting the time required to switch X-rays from the identified cardiac cycle.

20. The method as defined by claim 17, wherein:
controlling the X-ray data collecting system and the imaging table comprises controlling the X-ray data collecting system and the imaging table without synchronizing with either of the first cardiac phase coverage or the second cardiac phase coverage based on an electrocardiograph of the subject.

* * * * *